US008735351B2

(12) United States Patent
Murat Moreno et al.

(10) Patent No.: US 8,735,351 B2
(45) Date of Patent: May 27, 2014

(54) PHOSPHOLIPID-ENRICHED VESICLES BEARING TISSUE FACTOR HAVING HAEMOSTATIC ACTIVITIES AND USES THEREOF

(75) Inventors: Jesús Murat Moreno, Castelldefels (ES); Juan Ramon Rodriguez Fernández-Alba, Castelldefels (ES)

(73) Assignee: Thrombotargets Europe, S.L., Barcelona (ES)

( * ) Notice: Subject to any disclaimer, the term of this patent is extended or adjusted under 35 U.S.C. 154(b) by 53 days.

(21) Appl. No.: 13/642,491

(22) PCT Filed: Apr. 19, 2011

(86) PCT No.: PCT/EP2011/056219
§ 371 (c)(1),
(2), (4) Date: Nov. 19, 2012

(87) PCT Pub. No.: WO2011/131658
PCT Pub. Date: Oct. 27, 2011

(65) Prior Publication Data
US 2013/0059782 A1 Mar. 7, 2013

(30) Foreign Application Priority Data

Apr. 19, 2010 (EP) .................................. 10382085

(51) Int. Cl.
*A61K 38/36* (2006.01)
*A61P 9/00* (2006.01)
*G01N 33/86* (2006.01)
(52) U.S. Cl.
CPC ...................................... *A61K 38/36* (2013.01)
USPC ........... 514/13.3; 514/13.8; 514/13.7; 436/69
(58) Field of Classification Search
None
See application file for complete search history.

(56) References Cited

U.S. PATENT DOCUMENTS

| | | | |
|---|---|---|---|
| 5,591,616 A | 1/1997 | Hiei et al. | |
| 5,618,676 A | 4/1997 | Hitzeman et al. | |
| 5,622,931 A | 4/1997 | Edgington et al. | |
| 5,854,018 A | 12/1998 | Hitzeman et al. | |
| 5,856,123 A | 1/1999 | Hitzeman et al. | |
| 5,919,651 A | 7/1999 | Hitzeman et al. | |
| 6,130,074 A | 10/2000 | Brennan | |
| 6,596,712 B2 | 7/2003 | Zasloff et al. | |
| 2006/0046309 A1 | 3/2006 | Morrissey et al. | |
| 2006/0088524 A1 | 4/2006 | Morrissey et al. | |

FOREIGN PATENT DOCUMENTS

| | | | |
|---|---|---|---|
| EP | 0045573 A2 | 2/1982 | |
| EP | 0604662 A1 | 7/1994 | |
| EP | 1212420 B1 | 6/2005 | |
| EP | 1935902 A | 6/2008 | |
| EP | 1939218 A1 | 7/2008 | |
| WO | WO 98/48283 | * 10/1998 | ........... C07K 14/745 |
| WO | WO 9848283 A1 | * 10/1998 | |
| WO | WO9848283 A1 | 10/1998 | |
| WO | WO0121790 A1 | 3/2001 | |
| WO | WO0234109 A2 | 5/2002 | |
| WO | WO02101006 A2 | 12/2002 | |
| WO | WO03012035 A2 | 2/2003 | |
| WO | WO2006004675 A2 | 1/2006 | |
| WO | WO2008080989 A1 | 7/2008 | |

OTHER PUBLICATIONS del Conde, Tissue-factor-bearing microvesicles arise from lipid rafts and fuse with activated platelets to initiate coagulation, Blood. 2005; 106:1604-1611.*
International Search Report and Written Opinion of the International Searching Authority, Search Report, Application No. PCT/EP2011/056219 issued by the European Patent Office, Rijswijk, Netherlands, dated Jul. 21, 2011.
C. Fauli I Trillo, et al., tratado de Farmacia Galenica, Generalidades De Los Preparados De Aplicacion topica: Defincion y Clasificacion, pp. 44-47; see partial translation below. Farmacia F2000, (the year of publication is sufficiently earlier than the effective U.S. filing date and any foreign priority date so that the particular month of publication is not in issue) 1993 1st Edition, Luzán 5, S.A. of Ediciones, Madrid Spain.
C. Fauli I Trillo, et al., tratado de Farmacia Galenica, Generalidades De Los Preparados De Aplicacion topica: Defincion y Clasificacion, pp. 44-47; Partial translation for document above. Farmacia F2000, (the year of publication is sufficiently earlier than the effective U.S. filing date and any foreign priority date so that the particular month of publication is not in issue) 1993 1st Edition, Luzán 5, S.A. of Ediciones, Madrid Spain.
Marta Izquierdo Rojo, Ingenieria genetica y transferncia genica, Jun. 2004, pp. 10-11, 283-316, Ediciones Piramide, Madrid, Spain. See partial translation below.
Marta Izquierdo Rojo, Ingenieria genetica y transferncia genica, Jun. 2004, pp. 7-11, 284-316, Ediciones Piramide, Madrid, Spain. Partial translation for the document listed above.
United States Pharmacopeial Convention, Inc., USP XXII, NFXVII, the United States Pharmacopeia, The National Formulary, Jan. 1989, pp. 407-408, 802-803, 1255, 1961-1963, 1985, 2016-2017, 2024-2025, 2032-2033, 2044-2045, 2050-2051, 2054-2055, The Untied States Pharmacopeial Convention, Inc., Board of Trustees, Rockville, MD.

(Continued)

*Primary Examiner* — Jean Witz
*Assistant Examiner* — Mindy Newman
(74) *Attorney, Agent, or Firm* — Peter B. Scull; Hamilton, DeSanctis and Cha, LLP.

(57) ABSTRACT

The invention relates to a method for improving the procoagulant properties of TF expressed in eukaryotic cells by contacting microvesicles derived from said eukaryotic cells with a negatively-charged phospholipid such as phosphatidylserine. The invention also relates to microvesicles obtained using said method as well as to the uses thereof as procoagulant agents, for wound healing and for promoting angiogenesis.

17 Claims, 14 Drawing Sheets

(56) References Cited

OTHER PUBLICATIONS

M. Bacila, Biochemistry and Genetics of Yeasts, Pure and Applied Aspects, (J. Carbon, The Isolation and Characterization of Specific Gene Systems from the Yeast, *Saccharomyces cerevisiae*) (the year of publication is sufficiently earlier than the effective U.S. filing date and any foreign priority date so that the particular month of publication is not in issue) 1978, pp. 425-437, Academic Press, Inc., London, NY, Toronto, Sydney, San Francisco.

Notification of Transmittal of the International Preliminary Report on Patentability, Application No. PCT/EP2011/056219 issued by the European Patent Office, Munich, Germany, dated Aug. 16, 2012.

L. Mimms, et al., Phospholipid Vesicle Formation and Transmembrane Protein Incorporation Using Octyl Glucoside, Biochemistry, (the year of publication is sufficiently earlier than the effective U.S. filing date and any foreign priority date so that the particular month of publication is not in issue) 1981, pp. 833-840, vol. 20, No. 4, American Chemical Society, New York, NY, US.

F.A. Skinner, et al., Biology and Activities of Yeasts, The Society for Applied Bacteriology Symposium Series No. 9, (the year of publication is sufficiently earlier than the effective U.S. filing date and any foreign priority date so that the particular month of publication is not in issue) 1980, pp. ix, xi, x, xiii, xii, 2, No. 9, Academic Press, London, New York, Toronto, Sydney, San Francisco.

S. Altschul, et al., Basic Local Alignment Search Tool, Journal Molecular Biology, (the year of publication is sufficiently earlier than the effective U.S. filing date and any foreign priority date so that the particular month of publication is not in issue) 1990, pp. 403-410, vol. 215, Elsevier, Amsterdam, NL.

K. Terpe, Overview of Tag Protein Fusions: from Molecular and Biochemical Fundamentals to Commercial Systems, Appl Microbiol Biotechnol (2003), Nov. 2002, pp. 523-533, vol. 60, Springer-Verlag, New York, NY, US.

J. Sambrook, et al., Molecular Cloning, A Laboratory Manual, 3rd Edition, (the year of publication is sufficiently earlier than the effective U.S. filing date and any foreign priority date so that the particular month of publication is not in issue) 2001, pp. 4.67-4.69, 4.72-4.73, 4.70-4.71, vol. 1, Cold Spring Harbor Laboratory Press, Cold Spring Harbor, New York, NY, US.

G.J.H. Van Rooijen, et al., Structural Requirements of Oleosin Domains for Subcellular Targeting to the Oil Body, Plant Physiology, Sep. 1, 1995, pp. 1353-1361, vol. 109, American Society of Plant Biologists, Rockville, MD, US.

Jin-Hao Liu, et al., Plant Seed Oil-bodies as an Immobilization Matrix for a Recombinant Xylanase from the Rumen Fungus, Neocallimastix patriciarum, Molecular Breeding, Sep. 24, 1997, pp. 463-470, vol. 3, Kluwer Academic Publishers, Belgium.

N. V. Borisjuk, Production of Recombinant Proteins in Plant Root Exudates, Nature Biotechnology, May 1999, pp. 466-469, vol. 17, Nature America Inc., New York, NY, US.

E. E. Hood, et al., Commercial Production of Avidin from Transgenic Maize: Characterization of Transformant, Production, Processing, Extraction and Purification, Molecular Breeding, Apr. 7, 1997, pp. 291-306, vol. 3, Kluwer Academic Publishers, Belgium.

F. Shahidi, et al., Chemicals via Higher Plant Bioengineering (E. Hood, et al., Molecular farming of Industrial Proteins From transgenic Maize) Advances in Experimental Medicine and Biology, (the year of publication is sufficiently earlier than the effective U.S. filing date and any foreign priority date so that the particular month of publication is not in issue) 1999, pp. vii-viii, 127-147, vol. 464, Kluwer Academic/Plenum Publishers, New York, NY, US.

A. Kusnadi, et al., Production of Recombinant Proteins in Transgenic Plants: Practical Considerations, Biotechnology and Bioengineering, Dec. 5, 1997, pp. 473-484, vol. 56, No. 5, John Wiley & Sons, Inc., Hoboken, NJ, US.

A. Kusnadi, et al., Processing of Transgenic Corn Seed and Its Effect on the Recovery of Recombinant B-Glucuronidase, Biotechnology and Bioengineering, Oct. 5, 1998, pp. 44-52, vol. 60, No. 1, John Wiley & Sons, Inc., Hoboken, NJ, US.

A. Kusnadi, et al., Production and Purification of Two Recombinant Proteins from Transgenic Corn, Biotechnology Progress, (the year of publication is sufficiently earlier than the effective U.S. filing date and any foreign priority date so that the particular month of publication is not in issue) 1998, pp. 149-155, vol. 14, No. 1, John Wiley & Sons, Inc., Hoboken, NJ, US.

D. R. Witcher, et al., Commercial Production of B-glucuronidase (GUS): a Model System for the Production of Proteins in Plants, Molecular Breeding, (the year of publication is sufficiently earlier than the effective U.S. filing date and any foreign priority date so that the particular month of publication is not in issue) 1998, pp. 301-312, vol. 4, Kluwer Academic Publishers, Netherlands.

T. Verch, et al., Expression and Assembly of a Full-length Monoclonal Antibody in Plants Using a Plant Virus Vector, Journal of Immunological Methods, Jul. 30, 1998, pp. 69-75, vol. 220, Elsevier, Amsterdam, NL.

F. R. Brennan, et al., Chimeric Plant Virus Particles Administered Nasally or Orally Induce Systemic and Mucosal Immune Responses in Mice, Journal of Virology, Feb. 1999, pp. 930-938, vol. 73, No. 2, American Society of Microbiology, Washington, DC.

F. R. Brennan, et al., A Chimaeric Plant Virus Vaccine Protects Mice Against a Bacterial Infection, Microbiology, Apr. 1999, pp. 2061-2067, vol. 145, SGM, Great Britain.

T. Arakawa, et al., Expression of Cholera Toxin B submit Oligomers in Transgenic Potato Plants, Transgenic Research, Jun. 1997, pp. 403-413, Chapman & Hall, New York, NY.

T. Arakawa, et al., Efficacy of a Food Plant-Based Oral Cholera Toxin B Subunit Vaccine, Nature Biotechnology, Mar. 1998, pp. 292-297, vol. 16, Nature Publishing Group, London, England.

C.O. Tacket, et al., Immunogenicity in Humans of a Recombinant Bacterial Antigen Delivered in a Transgenic Potato, Nature Medicine, May 1998, pp. 607-609, vol. 4, No. 5, Nature Publishing Group, London, England.

R.T. Fraley, et al., Genetics, Expression of Bacterial Genes in Plant Cells, Proc. Natl. Acad. Sci. USA, Aug. 1983, pp. 4803-4807, vol. 80, Proceedings of the National Academy of Sciences of the USA, Washington, DC.

E. E. Hood, et al., Restriction Endonuclease Map of pTi Bo542, A Potential Ti Plasmid Vector for Genetic Engineering of Plants, Research Papers, Bio/Technology, Aug. 1984, pp. 702-709.

E. E. Hood, et al., T-DNA and Opine Synthetic Loci in Tumors Incited by *Agrobacterium tumefaciens* A281 on Soybean and Alfalfa Plants, Journal of Bacteriology, Dec. 1986, pp. 1283-1290, vol. 168, No. 3, American Society for Microbiology, Washington, D.C.

T. Komari, et al., Physical and Functional Map of Supervirulent *Agrobacterium tumefaciens* Tumor-Inducing Plasmid pTiB0542, Journal of Bacteriology, Apr. 1986, pp. 88-94, vol. 166, No. 1, American Society for Microbiology, Washington, D.C.

S. Jin, et al., Genes Responsible for the Supervirulence Phenotype of *Agrobacterium tumefaciens* A281, Journal of Bacteriology, Oct. 1987, pp. 4417-4425, vol. 169, No. 10, American Society for Microbiology, Washington, D.C.

T. Komari, Transformation of Callus Cultures of Nien Plant Species Mediated by *Agrobacterium*, Plant Science, Oct. 1989, pp. 223-229, vol. 60, Elsevier Scientific Publishers Ireland Ltd., Co Clare, Ireland.

pLB3A (ATCC 37394) Organism: Azotobacter vinelandii Lipman/ Tissue: Clone / Depositors: PE Bishop (References: Bishop PE, et al.; Molecular cloning of nif DNA from Azotobacter vinelandii, J. Bacteriol, 162: 21-28, 1985. PubMed: 3884589) (the year of publication is sufficiently earlier than the effective U.S. filing date and any foreign priority date so that the particular month of publication is not in issue).

A. Rose, et al., The Yeasts, Yeast Technology, Academic Press, (the year of publication is sufficiently earlier than the effective U.S. filing date and any foreign priority date so that the particular month of publication is not in issue) 1993, pp. 325-347, vol. 5, Second Edition, Academic Press, London, New York, Toronto, Sydney, San Francisco.

A. Hinnen, et al., Transformation of Yeast, Proc. Natl. Acad. Sci. USA, Apr. 1978, pp. 1929-1933, vol. 75, No. 4, Proceedings of the National Academy of Sciences of the USA, Washington, DC.

J. Beggs, et al., Transformatin of Yeast by a Replicating Hybrid Plasmid, Nature, Sep. 14, 1978, pp. 104-108, Macmillian Journals Ltd, London, England.

(56) References Cited

OTHER PUBLICATIONS

D. Becker, et al., High-Efficiency Transformation of Yeast by Electroporation, Methods in Enzymology, (the year of publication is sufficiently earlier than the effective U.S. filing date and any foreign priority date so that the particular month of publication is not in issue) 1991, pp. 182-187, vol. 194, Academic Press, Inc. London, New York, Toronto, Sydney, San Francisco.

D. Gietz, et al., Transformation of Yeast by Lithium Acetate/Single-Stranded carrier DNA/Polyethylene Glycol Method, Methods in Enzymology, (the year of publication is sufficiently earlier than the effective U.S. filing date and any foreign priority date so that the particular month of publication is not in issue) 2002, pp. 87-96, vol. 350, Elsevier Science (USA), Waltham, MA.

R.C. Mount, et al., Transformation of Lithium-Treated Yeast Cells and the Selection of Auxotrophic and Dominant Markers, from Methods in Molecular Biology, (the year of publication is sufficiently earlier than the effective U.S. filing date and any foreign priority date so that the particular month of publication is not in issue) 1996, pp. 139-145, vol. 53, Evans Humana Press Inc., Totowa, NJ.

T. Wang, et al., Transformation Systems of Non-Saccharomyces Yeasts, Critical Reviews in Biotechnology, (the year of publication is sufficiently earlier than the effective U.S. filing date and any foreign priority date so that the particular month of publication is not in issue) 2001, pp. 177-218, vol. 21, No. 3, CRC Press LLC, Boca Raton, FL.

P.J. Barr, et al., Yeast Genetic Engineering, A. Hinnen, et al., Chapter 10, Heterologous Gene Expression in Yeast, (the year of publication is sufficiently earlier than the effective U.S. filing date and any foreign priority date so that the particular month of publication is not in issue) 1989, pp. 193-212, Butterworths, London, United Kingdom.

D. W. Stanley-Samuelson, et al., Insect Lipids, Chemistry, Biochemistry & Biology, (the year of publication is sufficiently earlier than the effective U.S. filing date and any foreign priority date so that the particular month of publication is not in issue) 1993, pp. 27-33, University of Nebraska Press, Lincoln, NE.

K. Nakagawa, et al., The Angiogenic Effect of Tissue Factor on Tumors and Wounds, Seminars in Thrombosis and Hemostasis, (the year of publication is sufficiently earlier than the effective U.S. filing date and any foreign priority date so that the particular month of publication is not in issue) 1998, pp. 207-210, vol. 24, No. 23, Thieme Medical Publishers, New York, NY.

P. Philippart, et al., Human Recombinant Tissue Factor, Platelet-rich Plasma, and tetracycline Induce a High-Quality Human bone Graft: A 5-year Survey, The International Journal of Oral & Maxillofacial Implants (the year of publication is sufficiently earlier than the effective U.S. filing date and any foreign priority date so that the particular month of publication is not in issue) 2003, pp. 411-416, vol. 18, No. 3, Academy of Osseointegration, Arlington Heights, IL.

P. Carmeliet, et al., Role of Tissue Factor in Embryonic Blood Vessel Development, Nature, Sep. 5, 1996, pp. 73-75, vol. 383, Macmillian Journals Ltd, London, England.

T. H. Bugge, et al., Fatal Embryonic Bleeding Events in Mice Lacking Tissue Factor, the Cell-associated Initiator of Blood Coagulation, Proc. Natl. Acad. Sci. USA, Medical Sciences, Jun. 1996, pp. 6258-6263, vol. 93, Proceedings of the National Academy of Sciences of the USA, Washington, DC.

J.R. Toomey, et al., Targeted Disruption of the Murine Tissue Factor Gene Results in Embryonic Lethality; Blood, from bloodjournal.hematologylibrary.org at CSIC on Dec. 18, 2012, pp. 1583-1587, vol. 1996, No. 88, The American Society of Hematology, Washington, D.C.

D. Richard, et al., Angiogenesis and G-Protein Recptors: Signals that Bridge the Gap, Oncogene, (the year of publication is sufficiently earlier than the effective U.S. filing date and any foreign priority date so that the particular month of publication is not in issue) 2001, pp. 1556-1562, vol. 20, Nature Publishing Group, London, England.

A. F. Milia, et al., Protease-Activated Receptor-2 Stimulates Angiogenesis and Accelerates Hemodynamic Recovery in a Mouse Model of Hindlimb Ischemia, Circulation Research, Journal of the American Heart Association, website accessed on Dec. 18, 2012, http://circres.ahahournals.org, Dallas, TX.

B. M. Mueller, et al., Expression of Tissue Factor by Melanoma Cells Promotes Efficient Hematogenous Metastasis, Proc. Natl. Acad. Sci. USA, Immunology, Dec. 1992, pp. 11832-11836, vol. 89, Proceedings of the National Academy of Sciences of the USA, Washington, DC.

G. C. White, et al., Chapter 65, Approach to the Bleeding Patient, Hemostasis and Thrombosis, Basic Principles and Clinical Practices, Coleman, et al., (the year of publication is sufficiently earlier than the effective U.S. filing date and any foreign priority date so that the particular month of publication is not in issue) 1987, pp. 1048-1060, J. B. Lippencott Co., Philadelphia, PA.

J. Hirsh, M.D., Mechanism of Action and Monitoring of Anticoagulants, Seminars in Thrombosis and Hemostasis, 9the year of publication is sufficiently earlier than the effective U.S. filing date and any foreign priority date so that the particular month of publication is not in issue) 1986, pp. 1-11, vol. 12, No. 1, Thieme Inc., New York, NY.

R. A. O'Reilly, Chapter 90, Section D, Therapeutic Modalities for Thrombotic Disorders, Vitamin K Antagonists, Hemostasis and Thrombosis, Basic Principles and Clinical Practices, Coleman, et al., (the year of publication is sufficiently earlier than the effective U.S. filing date and any foreign priority date so that the particular month of publication is not in issue) 1987, pp. 1367-1372, J. B. Lippencott Co., Philadelphia, PA.

R. Bach, et al., Factor VII Binding to Tissue Factor in Reconstituted Phospholipid Vesicles: Induction of Cooperativity by Phosphatidylserine, Biochemistry, (the year of publication is sufficiently earlier than the effective U.S. filing date and any foreign priority date so that the particular month of publication is not in issue) 1986, pp. 4007-4020, vol. 25, No. 14, American Chemical Society, New York, NY.

R. Bach, et al., Expression of Tissue Factor Procoagulant Activity: Regulation by Cytosolic Calcium, Proc. Natl. Acad. Sci. USA, Cell Biology, Sep. 1990, pp. 6995-6999, vol. 87, No. 18, Proceedings of the National Academy of Sciences of the USA, Washington, DC.

C. L. Brucato, et al., Expression of Recombinant Rabbit Tissue Factor in *Pichia pastoris*, and its Application in a Prothrombin Time Reagent, Protein Expression and Purification, Dec. 2002, pp. 386-393, vol. 26, No. 3, Academic Press, San Diego, CA.

\* cited by examiner

A

B

Healthy plasma

Hemophilic plasma

C

D

SEQUENCE LISTING

```
<160> NUMBER OF SEQ ID NOS: 8

<210> SEQ ID NO 1
<211> LENGTH: 263
<212> TYPE: PRT
<213> ORGANISM: Homo sapiens
```

```
<400> SEQUENCE: 1

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu Ile Phe Tyr Ile Ile
210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
                245                 250                 255

Asn Ser Pro Leu Asn Val Ser
            260

<210> SEQ ID NO 2
<211> LENGTH: 6
<212> TYPE: PRT
<213> ORGANISM: Artificial
<220> FEATURE:
<223> OTHER INFORMATION: Epitope AHGHRP

<400> SEQUENCE: 2

Ala His Gly His Arg Pro
1               5

<210> SEQ ID NO 3
<211> LENGTH: 14
<212> TYPE: PRT
<213> ORGANISM: Artificial
<220> FEATURE:
<223> OTHER INFORMATION: Epitope PIHDHDHPHLVIHS

<400> SEQUENCE: 3

Pro Ile His Asp His Asp His Pro His Leu Val Ile His Ser
1               5                   10
```

```
<210> SEQ ID NO 4
<211> LENGTH: 7
<212> TYPE: PRT
<213> ORGANISM: Artificial
<220> FEATURE:
<223> OTHER INFORMATION: Epitope GMTCXXC
<220> FEATURE:
<221> NAME/KEY: misc_feature
<222> LOCATION: (5)..(6)
<223> OTHER INFORMATION: Xaa can be any naturally occurring amino acid

<400> SEQUENCE: 4

Gly Met Thr Cys Xaa Xaa Cys
1               5

<210> SEQ ID NO 5
<211> LENGTH: 269
<212> TYPE: PRT
<213> ORGANISM: Artificial
<220> FEATURE:
<223> OTHER INFORMATION: Human mature TF with N124A mutation and C
      terminal hexahistidine tag

<400> SEQUENCE: 5

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Ala Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Ile Phe Tyr Ile Ile
    210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
                245                 250                 255

Asn Ser Pro Leu Asn Val Ser His His His His His His
            260                 265
```

```
<210> SEQ ID NO 6
<211> LENGTH: 813
<212> TYPE: DNA
<213> ORGANISM: Artificial
<220> FEATURE:
<223> OTHER INFORMATION: DNA encoding human mature TF with N124A and
      C-terminal hexahistidine tag

<400> SEQUENCE: 6
atgtcaggca ctacaaatac tgtggcagca tataatttaa cttggaaatc aactaatttc      60
aagacaattt tggagtggga acccaaaccc gtcaatcaag tctacactgt tcaaataagc     120
actaagtcag agattggaa aagcaaatgc ttttacacaa cagacacaga gtgtgacctc      180
accgacgaga ttgtgaagga tgtgaagcag acgtacttgg cacgggtctt ctcctacccg     240
gcagggaatg tggagagcac cggttctgct ggggagcctc tgtatgagaa ctccccagag     300
ttcacacctt acctggagac aaacctcgga cagccaacaa ttcagagttt tgaacaggtg     360
ggaacaaaag tggcagtgac cgtagaagat gaacggactt tagtcagaag gaacaacact     420
ttcctaagcc tccgggatgt ttttggcaag gacttaattt atacacttta ttattggaaa     480
tcttcaagtt caggaaagaa aacagccaaa acaaacacta atgagttttt gattgatgtg     540
gataaaggag aaaactactg tttcagtgtt caagcagtga ttccctcccg aacagttaac     600
cggaagagta cagacagccc ggtagagtgt atgggccagg agaaagggga attcagagaa     660
atattctaca tcattggagc tgtggtattt gtggtcatca tccttgtcat catcctggct     720
atatctctac acaagtgtag aaaggcagga gtggggcaga gctggaagga gaactcccca     780
ctgaatgttt cacatcacca tcaccatcac tag                                   813

<210> SEQ ID NO 7
<211> LENGTH: 39
<212> TYPE: DNA
<213> ORGANISM: Artificial
<220> FEATURE:
<223> OTHER INFORMATION: Oligonucleotide A

<400> SEQUENCE: 7
ccgctcgagc ggttatgaaa cattcagtgg ggagttctc                              39

<210> SEQ ID NO 8
<211> LENGTH: 36
<212> TYPE: DNA
<213> ORGANISM: Artificial
<220> FEATURE:
<223> OTHER INFORMATION: Oligonucleotide B

<400> SEQUENCE: 8
ccgctcgagc ggttattctc tgaattcccc tttctc                                 36
```

PHOSPHOLIPID-ENRICHED VESICLES BEARING TISSUE FACTOR HAVING HAEMOSTATIC ACTIVITIES AND USES THEREOF

FIELD OF THE INVENTION

The present invention refers, in general, to the treatment of haemorrhages and wound healing in a subject using a pro-coagulant agent based on tissue factor. More specifically, the invention relates to a Tissue Factor-bearing microvesicle (TF-bearing microvesicle) comprising an eukaryotic cell-derived membrane in the form of a microvesicle and a tissue factor protein and a negatively charged phospholipid (NCP) as well as to the applications thereof as a pro-coagulant agent useful for treating haemorrhages in a subject as well as for promoting angiogenesis and cell migration. The invention further relates to processes for the production of said TF-bearing microvesicles.

BACKGROUND OF THE INVENTION

Hemostasis is the mechanism by means of which living beings respond to a haemorrhage and involves the participation of two processes that become functional immediately after a lesion and remain active for a long period of time. The first of them is known as primary hemostasis and is characterized by the occurrence of vasoconstriction at the vascular lesion site and platelet aggregate formation. The second one is known as secondary hemostasis, being the phase in which the fibrin clot is formed due to the action of the different coagulation cascade proteolytic enzymes.

Several cofactors and proteolytic enzymes participate in the second phase of the blood coagulation process, all referred to as coagulation factors, and it consists of several phases ending with fibrin formation from fibrinogen hydrolysis due to the action of thrombin. Thrombin is previously formed by proteolytic hydrolysis of an apoenzyme, pro-thrombin. This proteolysis is carried out by the activated coagulation Factor X (FXa), which binds to the surface of the activated platelets and only in the presence of its cofactor, activated coagulation Factor V (FVa), and calcium ions, and is able to hydrolyze prothrombin. Coagulation Factor X (FX) activation can occur in two separate pathways, the intrinsic pathway and the extrinsic pathway.

The intrinsic pathway consists of a series of reactions in which each proenzyme is hydrolyzed, yielding its active protease form. In each step, the recently formed proteolytic enzyme will catalyze activation of the following proenzyme to successively yield the active form.

In the blood coagulation extrinsic pathway, the Tissue Factor (TF), exposed on adventitia cells at the lesion site, binds to circulating coagulation Factor VII/activated coagulation Factor VII (FVII/FVIIa) to form the TF::FVIIa complex and, in the presence of calcium, to act as a substrate so that FX activation takes place. The extrinsic pathway is currently considered the most relevant pathway in blood coagulation, and it is accepted that in the event of a hemorrhage produced by a vascular lesion, coagulation is triggered due to extrinsic pathway activation involving the interaction of TF with its ligand, FVII/FVIIa.

It has been broadly accepted that TF is the main element responsible for the quickness with which coagulation is initiated, and it is required for FX activation, which in turn begins prothrombin hydrolysis.

Purification of TF has been reported from various tissues such as: human brain, bovine brain; human placenta; ovine brain; and lung. It is widely accepted that while there are differences in structure of TF protein between species there are no functional differences as measured by in vitro coagulation assays.

It is widely accepted that in order to show biological activity, TF must be associated with phospholipids in vitro. It has been shown that the removal of the phospholipid component of TF, for example by use of a phospholipase, results in a loss of its biological activity in vitro.

WO2008080989 describes tissue factor-bearing yeast derived microvesicles comprising a yeast membrane and a tissue factor protein and the use thereof as pro-coagulant agents in the treatment of hemorrhages in a subject.

WO2006004675 describes the expression of tissue factor in plant cells, crude extracts obtained from plants expressing TF and artificial vesicles comprising recombinant TF obtained from plant cells.

EP19359021 describes the expression of tissue factor in insect cells as well as relipidated TF which contains recombinant TF expressed in insect cells.

However, there is a need in the art for additional pro-coagulant preparations based on TF.

SUMMARY OF THE INVENTION

In a first aspect, the invention relates to a method for the preparation of a TF-bearing microvesicle having pro-coagulant activity comprising
  (i) expressing TF or a variant thereof having pro-coagulant activity in an eukaryotic cell,
  (ii) recovering TF-bearing microvesicles from the cells of step (i) and
  (iii) contacting the vesicles obtained in step (ii) with a negatively charged phospholipid under conditions adequate for the incorporation of said phospholipid into said vesicles.

In a second aspect, the invention relates to a method for the preparation of a TF-bearing microvesicle having pro-coagulant activity which comprises:
  (i) providing lipid microvesicles obtained from an eukaryotic cell,
  (ii) contacting a TF protein or a variant thereof having pro-coagulant activity with lipid microvesicles as defined in (i) under conditions adequate for the incorporation of said TF protein or variant thereof into said microvesicles and
  (iii) contacting the vesicles obtained in step (ii) with a negatively charged phospholipid under conditions adequate for the incorporation of said phospholipids into said vesicle,
wherein steps (ii) and (iii) can be carried out in any order.

In another aspect, the invention relates to a TF-bearing microvesicle obtained using the method of the invention.

In yet another aspect, the invention relates to a pharmaceutical composition comprising a TF-bearing microvesicle of the invention and a pharmaceutically acceptable vehicle.

In another aspect, the invention relates to a pharmaceutical composition comprising
  (i) a microvesicle obtained by a method comprising the steps of
    a) expressing TF or a functionally equivalent variant thereof having pro-coagulant activity in an eukaryotic cell and
    b) recovering TF-bearing microvesicles from the cells of step (a),
  (ii) at least a coagulation promoter and
  (iii) a pharmaceutically effective vehicle In another aspect, the invention relates to a TF-bearing microvesicle of the invention or to a pharmaceutical composition of the invention for use as a medicament.

In another aspect, the invention relates to a TF-bearing microvesicle of the invention or to a pharmaceutical composition of the invention for use in the treatment of a haemorrhage, for promoting wound healing or for the treatment of an angiogenesis-related disease.

In another aspect, the invention relates to the use of a TF-bearing microvesicle of the invention for the determination of the prothrombin time in a sample.

In another aspect, the invention relates to a kit for the determination of an anticoagulant therapy factor comprising a microvesicle of the invention.

DETAILED DESCRIPTION OF THE INVENTION

Figure 1:
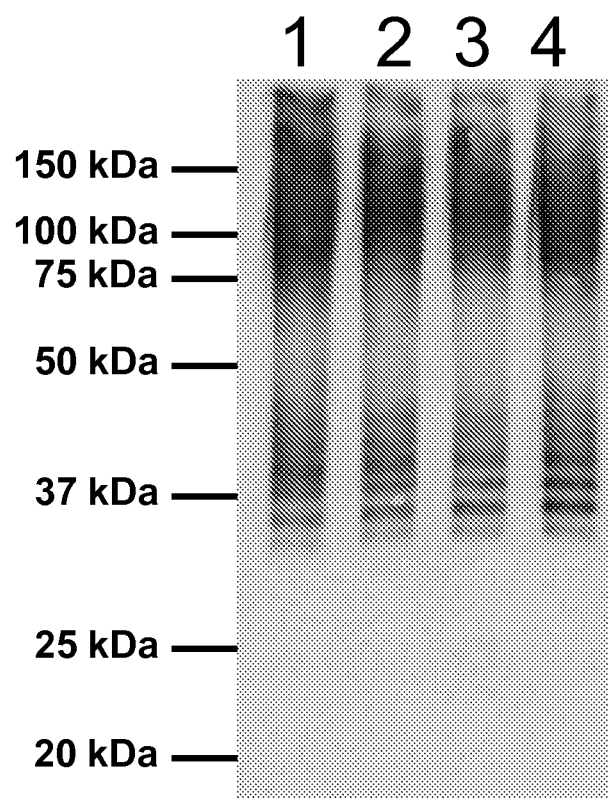
FIG. 1 Expression of the rTF by the TT-173 extracts. Western-blot analyses of extracts from purified TT-173 (MFR 0.1) from four independent tangential flow filtrations. Blot was reacted with human purified mouse antibody (BD Biosciences Pharmingen). Molecular weight markers in kDa are shown at the left side of the figure.

The inventors have found that the addition of extra phosphatidylserine (PS) in the absence of detergents to a TF-bearing microvesicles derived from yeast cells and already containing PS, surprisingly results in improved pro-coagulant properties of said vesicles as well as in an increased stability of said vesicles. The increased procoagulant properties can be observed, for instance, in the experiments shown in examples 2 and 3 of the present invention, wherein it is clearly shown that the addition of phosphatidylserine to yeast-derived microvesicles comprising TF results in vesicles showing increased pro-coagulant properties (reduced coagulation time) with respect to vesicles which have not been contacted with the phospholipid (see e.g. FIG. 2 and table 2). Without wishing to be bound by any theory, it is believed that PS interacts with the TF-bearing microvesicles resulting in an increased capability of the vesicles to recruit plasmatic factors involved in the formation of both, prothrombinase and Xase complexes, which in turns leads to an increased production of thrombin. The increased stability of the vesicles is shown, for instance, in example 4 of the present invention, wherein it is shown that vesicles pretreated with PS show increased stability at both 20° C. and 4° C.

First Method of the Invention

In a first aspect, the invention relates to a method (hereinafter first method of the invention) for the preparation of a TF-bearing microvesicle having pro-coagulant activity which comprises:
(i) expressing TF or a variant thereof having pro-coagulant activity in an eukaryotic cell,
(ii) recovering TF-bearing microvesicles from the cells of step (i) and
(iii) contacting the microvesicles obtained in step (ii) with a negatively charged phospholipid (NCP) under conditions adequate for the incorporation of said phospholipid into said microvesicles.

As used herein, the term "TF-bearing microvesicle" refers to any lipid microvesicle that contains TF integrated in said lipid microvesicle and which derives from an eukaryotic cell. Lipid microvesicle refers to a small and closed compartment, which is substantially composed by lipids mono or bilayers. The size of the TF-bearing microvesicle of the invention can vary within a relatively broad range, usually, said size is equal to or lower than 10 μm, typically equal to or lower than 0.5 μm. In a particular embodiment, the size of the TF-bearing yeast derived microvesicles of the invention range from 10 to 0.01 μm.

The microvesicles are formed by lipid membranes, or fragments thereof, from eukaryotic cells. A membrane refers, in general, to an organized layer of a few molecules (lipids and proteins) thick forming the boundary of a cell (i.e., the cell or plasma membrane) or the boundaries of intracellular organelles. Typically a membrane is composed of two oriented lipid layers (i.e., a lipid bilayer) in which proteins can be embedded. A lipid bilayer, which is the basic structure of the membranes of a cell, is usually formed by amphipathic molecules (e.g. phospholipids, fatty acids etc.) in an aqueous environment, each molecule being oriented with the hydrophilic group on the outside of the layer and the hydrophobic group to the interior of the layer.

In a first step, the first method of the invention, comprises the expression TF or a variant thereof having pro-coagulant activity in a eukaryotic cell As "eukaryotic cell" is referred in the present invention as any cells that contain complex structures enclosed within membranes like a nucleus. Examples eukaryotic cells that can be used in the first method of the invention are fungi cells, yeast cells, plant cells and animal cells (like a mammalian cell, a fish cell, a reptile cell, an insect cell, etc).

As used herein, the term "yeast cells" includes any ascosporogenous yeasts (Endomycetales), basidiosporogenous yeasts, and yeast belonging to the Fungi Imperfecti (Blastomycetes) Since the classification of yeast may change in the future, for the purposes of this invention, yeast shall be defined as described in described by Skinner, F. et al, (Biology and Activities of Yeast, Soc. App. Bacteriol. Symp. Series No. 9). Suitable yeast strains include, without limitation, any species of Torula, baker's yeast, brewer's yeast, a *Saccharomyces* species such as *S. cerevisiae*, a *Schizosaccharomyces* species, a *Pichia* species such as *Pichia pastoris*, a *Candida* species, a *Hansenula* species such as *Hansenula polymorphs*, and a *Klyuveromyces* species such as *Klyuveromyces lactis* as well as the different strains from the above mentioned yeast species, such as the *S. cerevisiae* T73 strain. Also mixture of any of these species and strains might be used.

As used herein, the term "plant cells" includes cells from plants, including, but not limited to, algae, monocots, dicots, and, specifically, cereals (e.g., maize, rice, oat, etc.), legumes (e.g., soy, etc.), cruciferous (e.g., *Arabidopsis thaliana*, colza, etc.) or solanaceous (e.g., potato, tomato, tobacco, etc.). Plant cells include suspension cultures, embryos, merstematic regions, callus tissue, leaves, roots, shoots, gametophytes, sporophytes, pollen, seeds and microspores. As a person skilled in the art would understand the plant cell can be part of a plant or a whole plant thus referring as a "plant host system". The "plant host system" or the isolated plant cells may be at various stages of maturity. Plant host system also refers to any clone of such plant, seed, selfed or hybrid progeny, propagule whether generated sexually or asexually, and descendants of any of these, such as cuttings or seeds.

As used herein, the term "animal cells" includes any cell from an animal. Animal cells include mammalian cells, fish cells, reptile cells, insect cells, etc. The animal cells can be derived from any tissue of the animal (primary culture cells) or can be immortalized cells. Immortalized cells can be obtained from tumor tissues or be immortalized using techniques known by the person skilled such as infection with viruses (e.g. EP1212420) or the fusion of normal cells with an immortalized cell line.

Insect cells include, without being limited to, Sf9 cells, SF21 cells, SF+ cells, Hi-Five cells, or insect larval cells.

Mammals from which cells can be obtained include rats, mice, monkey, human, etc. Mammalian cells suitable for the present invention include epithelial cell lines, osteosarcoma cell lines, cell lines of neuroblastoma, epithelial carcinomas, glial cells, liver cell lines, CHO (Chinese Hamster Ovary) cells, COS cells, BHK cells, HeLa cells, 911 cells, AT1080 cells, A549 cells, 293 cells or PER.C6 cells, human ECC NTERA-2 cells, D3 cells of the mESC line, human embryonic stem cells such as HS293 and BGV01, SHEF1, SHEF2 and HS181, NIH3T3 cells, 293T cells, REH cells and MCF-7 cells and hMSC cells.

The term "tissue factor" or "TF", also known as "thromboplastin", "platelet tissue factor", "CD142" or "coagulation factor III", as used herein, refers to an integral membrane glycoprotein that is widely distributed in the animal kingdom, which appears in the subendothelial tissue, platelets, and leukocytes and is necessary for the initiation of thrombin formation from the zymogen prothrombin. Suitable TF polypeptides for use in the present invention include native or wild-type (wt) TF of any animal species, including humans. Exemplary TF proteins that can be used in the present invention include human TF (UniProtKB accession number P13726), mouse TF (UniProtKB accession number P20352), rat TF (UniProtKB accession number P42533), pig TF (NCBI Prot Accession number NP_998950), bovine TF (NCBI Prot Accession number AAB20755), dog TF (NCBI Prot Accession number BAD98568), guinea pig TF (NCBI Prot Accession number AAF36523) and TF proteins of different organisms.

Since native TF contains several glycosylation sites, TF variants showing different degrees of glycosylation can be obtained by expressing TF in hosts capable of carrying out N-glycosylation reactions. Mature TF contains three potential N-linked glycosylation having the consensus sequence Asn-Xaa-Ser/Thr located at Asn11 (sequence Asn11-Leu12-Thr13), Asn124 (sequence Asn124-Val125-Thr126) and Asn137 (sequence Asn137-Asn138-Thr139). Thus, TF molecules for use in the present invention include TF variants having a variable degree of N-linked glycosilation in one or more N-glycosylation sites. In yeast, glycosylation typically involves an inner core of about ten mannose residues, linked to the asparagine via two GlcNAc residues, and a branched outer chain of 50-100 mannose residues. Therefore N-linked glycosylation could potentially add as many as 300 mannose residues to TF, an increase in molecular mass in about 60 kDa. In addition, it is also possible that several mannose residues could be attached to various (more than 25) O-linked glycosylation sites. In a particular embodiment, the TF-bearing yeast derived microvesicule of the invention comprises a glycosylated TF protein. As used herein the term "glycosylated" includes any degree of glycosylation.

The term "variant of TF having pro-coagulant activity" refers to compounds showing substantially the same biological activity(ies) as TF and resulting from the insertion, deletion, or substitution of one or more amino acid residues. Suitable functional assays that can be used to assess whether a given polypeptide is a functionally equivalent variant of TF are those assays based on the determination of the ability of the TF variant to specifically bind FVIIa, or based on the in vitro determination of the coagulation time in plasma or whole blood, by an in vivo assay in a severe hemorrhage animal model or by an in vivo assay in a lethal hemorrhage animal model. Procedures for carrying out these assays has been described in the prior art and are summarized in the examples of the present invention (Section "Methods") as well as in the application WO2008080989.

Variants according to the present invention include amino acid sequences that are at least 60%, 70%, 80%, 90%, 95% or 96% similar or identical to the native TF molecules mentioned above. As known in the art the "similarity" between two proteins is determined by comparing the amino acid sequence and its conserved amino acid substitutes of one protein to a sequence of a second protein. The degree of identity between two proteins is determined using computer algorithms and methods that are widely known for the persons skilled in the art. The identity between two amino acid sequences is preferably determined by using the BLASTP algorithm [BLASTManual, Altschul, S., et al., NCBI NLM NIH Bethesda, Md. 20894, Altschul, S., et al., J. Mol. Biol. 215: 403-410 (1990)].

The TF protein has a well-defined domain structure which comprises (1) a signal peptide or a region with a 32 amino acid leader sequence that is post-translationally processed when the protein is processed from the immature to the mature form; (2) an N-glycosylated hydrophilic extracellular domain comprising about 219 terminal amino acids; (3) a fragment of about 23 amino acids, mainly hydrophobic, which is believed to form the transmembrane domain amino acids; and (4) the 21-amino acid carboxyl end which is believed to be the amino acids forming part of the protein cytoplasmic fragment. The domain structure of the hTF protein allows the production of, for example, the extracellular domain of the protein or functional fragments thereof.

In a particular embodiment, the fragment of TF having pro-coagulant activity comprises a mature TF protein. The term "mature TF" as used herein, refers to the TF protein which amino acid sequence lacks the signal peptide. In a preferred embodiment, said mature TF protein comprises the human mature TF protein. Further, in a specific embodiment, said human mature TF protein has the amino acid sequence shown in SEQ ID NO: 1.

The fragment of TF protein having pro-coagulant activity may be glycosylated, partially glycosylated or non-glycosylated. Thus, in a particular embodiment, the TF-bearing lipid microvesicule of the invention comprises a non-glycosylated fragment of TF protein having pro-coagulant activity, whereas in another particular embodiment, said TF-bearing yeast derived microvesicule of the invention comprises a glycosylated fragment of TF protein having pro-coagulant activity. As mentioned above, the term "glycosylated" includes any degree of glycosylation. In a preferred embodiment, the TF or the functional variant thereof having pro-coagulant activity contains at least one non-functional N-glycosylation site.

In a preferred embodiment, the N-glycosylation site or sites are those corresponding to the N-glycosylation sites NLT at positions 11-13, NVT at positions 124-126 or NNT at positions 137-139 in the in the mature human TF. In a more preferred embodiment, the TF carries one or more substitutions of the Asn residues into residues which are not acceptors for N-glycosylation. In a still more preferred embodiment, the TF variant comprises one or more Asn-to-Ala mutations in the Asn residues in positions corresponding to positions 11, 124 or 137 in the mature human TF.

The glycosylation will vary depending of the expression system used for the production of the TF bearing lipid vesicles. Thus, the invention provides a recombinant mammalian tissue factor protein that includes at least one plant-specific glycan, yeast-specific glycan or animal-specific glycan.

In addition, as in the case of the TF protein, the fragment of TF protein having pro-coagulant activity used in carrying out this invention may be a member of a fusion protein, said fusion protein containing a first region comprising said TF protein fragment thereof having pro-coagulant activity, bound to a second region comprising another peptide or protein. Said second region may be bound to the amino-terminus region of said TF protein fragment, or, alternatively said second region may be bound to the carboxyl-terminus region of said TF protein fragment. Both first and second regions may be directly bound or bound through a linker polypeptide between said first and second regions.

In a particular embodiment, said fusion protein comprises a fragment of TF protein having pro-coagulant activity and a tag bound to the C-terminal or N-terminal domain of said TF protein fragment. Said tag is generally a peptide or amino acid sequence which can be used in the isolation or purification of said fusion protein. Illustrative, non-limitative examples of tags suitable for the production of this fusion protein include those mentioned previously in connection with the fusion protein wherein the first region was a TF protein. In a particular embodiment, said tag is a His-tag bound to the C-terminal domain of said TF protein or fragment thereof having pro-coagulant activity. In another embodiment, said tag is a His-tag bound to the N-terminal domain of said TF protein or fragment thereof having pro-coagulant activity. In a particular embodiment, the fusion protein comprises a mature TF protein, preferably, human mature TF protein. This fusion protein also has pro-coagulant activity, the pro-coagulant activity thereof can be assayed as previously mentioned, e.g., by any of the coagulation assays mentioned in Example 2.

In addition, the TF protein may be provided forming part of a fusion protein, said fusion protein containing a first region comprising the TF protein connected to a second region comprising another peptide or protein. Said second region may be bound to the amino-terminus region of said TF protein, or, alternatively said second region may be bound to the carboxyl-terminus region of said TF protein. Both first and second regions may be directly bound to each other or may be bound through a linker polypeptide between said first and second regions.

In a particular embodiment, said fusion protein comprises a TF protein and a tag, usually a peptide tag, bound to the C-terminal or N-terminal domain of said TF protein. Said tag is generally a peptide or amino acid sequence which can be used in the isolation or purification of said fusion protein. Thus, said tag is capable of binding to one or more ligands, such as, for example, one or more ligands of an affinity matrix such as a chromatography support or bead with high affinity. An example of said tag is a histidine tag (His-tag or HT), such as a tag comprising 6 residues of histidine (His6 or H6), which can bind to a column of nickel (Ni2+) or cobalt (Co2+) with high affinity. His-tag, as shown in Examples 1 (FIG. 4), has the desirable feature that it can bind its ligands under conditions that are denaturing to most proteins and disruptive to most protein-protein interactions. Thus, it can be used to remove the bait protein tagged with H6 following the disruption of protein-protein interactions with which the bait has participated.

Additional illustrative, non-limitative, examples of tags useful for isolating or purifying a fusion protein include Arg-tag, FLAG-tag, Strep-tag, an epitope capable of being recognized by an antibody, such as c-myc-tag (recognized by an anti-c-myc antibody), SBP-tag, S-tag, calmodulin binding peptide, cellulose binding domain, chitin binding domain, glutathione S-transferase-tag, maltose binding protein, NusA, TrxA, DsbA, Avi-tag, etc. (Terpe K., Appl. Microbiol. Biotechnol. (2003), 60:523-525), an amino acid sequence such as Ala-His-Gly-His-Arg-Pro (SEQ ID NO:2); Pro-Ile-His-Asp-His-Asp-His-Pro-His-Leu-Val-Ile-His-Ser (SEQ ID NO:3); Gly-Met-Thr-Cys-X-X-Cys (SEQ ID NO:4); β-galactosidase and the like.

In a particular embodiment, said tag is a His-tag bound to the C-terminal domain of said TF protein. In another embodiment, said tag is a His-tag bound to the N-terminal domain of said TF protein.

In a particular embodiment the fusion protein comprises a human TF lacking the signal sequence or the variant thereof having pro-coagulant activity which has a N124A mutation at the glycosilation site and an hexahistidine tag at the C terminus and is given by (SEQ ID NO: 5)

Said fusion protein may be obtained by conventional means, e.g., by means of gene expression of the nucleotide sequence encoding for said fusion protein in a suitable yeast cell. The eventual tag can be used, if desired, for the isolation or purification of said fusion protein.

In another particular embodiment, the first step of the first method of the invention involves the expression in the eukaryotic cell of a fragment of TF having pro-coagulant activity.

According to the invention, a portion of said TF protein or fragment thereof having pro-coagulant activity is integrated in said lipid membrane. Normally, said portion comprises the lipophilic region of said protein or fragment (i.e., the central domain of TF), whereas the hydrophyllic regions thereof (i.e., the amino-terminus region and the carboxyl-terminus region of said TF protein) face the exoplasmic or the endoplasmic side of the membrane. Information concerning the lipophilic and hydrophylic regions of TF protein can be obtained from WO2008080989. In a particular embodiment, the N-terminal domain of the TF protein or of the fragment thereof having pro-coagulant activity faces the exoplasmic side of said membrane, whereas in another particular embodiment the N-terminal domain of said TF protein or fragment having pro-coagulant activity faces the endoplasmic side of said membrane.

The method of expression of TF or a variant thereof depends of the eukaryotic cell used. Generally, the eukaryotic cell is transformed with a expression vector comprising the nucleotide sequence coding for TF protein or a fragment thereof having pro-coagulant activity, operatively linked to a functional promoter in any of the cells that can be used in the present invention: fungi, yeast, plant or animal (fish, reptilian, mammalian, insect, etc) cells.

The cDNA coding for TF protein or a fragment thereof having pro-coagulant activity can be amplified by the polymerase chain reaction (PCR) using a cDNA library as template and the appropriate primers. Example 1 discloses the amplification of the cDNA coding for the mature hTF protein with 18 extra nucleotides (coding for six histidines) at the 3' end.

A "vector", as used herein, refers to a nucleic acid molecule capable of transporting another nucleic acid to which it has been linked. The term "yeast expression vector", as used herein refers to DNA expression constructs, e.g., nucleic acid segments, plasmids, cosmids, phages, viruses or virus particles capable of synthesizing the subject proteins encoded by their respective recombinant genes (i.e., TF protein or a fragment thereof having pro-coagulant activity) carried by the vector in a yeast. Alternatively, nucleic acid segments may also be used to create transgenic yeast cells, using non-directional or homologous recombination, in which the gene or genes of interest are stably integrated into the yeast genome. Normally, the yeast expression vector comprises the nucleotide sequence coding for TF or a fragment thereof having pro-coagulant activity operatively linked to a promoter which is functional in yeast cells (i.e., a yeast-functional promoter). Vectors for use with the invention are, for example, vectors capable of autonomous replication and/or expression of nucleic acids to which they are linked in yeast cells. In the present specification, the terms "plasmid" and "vector" are used interchangeably as the plasmid is the most commonly used form of a vector. Moreover, the invention is intended to include such other forms of expression vectors that serve equivalent functions and which become known in the art subsequently hereto. Said yeast expression vector may be a yeast episomal expression vector or a yeast integrative expression vector, and they can be obtained by conventional techniques known for the skilled person in the art.

Thus, in an embodiment, said yeast expression vector is a yeast episomal expression vector. The term "yeast episomal expression vector" as used herein refers to an expression vector that is maintained as an extra-chromosomal DNA molecule in the yeast cytoplasm. In a particular embodiment, said yeast episomal expression vector, in addition to the nucleotide sequence coding for TF protein or a fragment thereof having pro-coagulant activity operatively linked to a yeast-functional promoter, further comprises: (i) a yeast selection gene; (ii) a yeast replication origin; (iii) a bacterial selection gene; and (iv) a yeast transcription termination signal. Advantageously, said yeast episomal expression vector further comprises a unique restriction site for cloning the selected gene (TF protein or a fragment thereof having pro-coagulant activity) under the control of the yeast-functional promoter and followed by the yeast transcription termination signal.

Practically any yeast-functional promoter, yeast selection gene, yeast replication origin, bacterial selection gene, yeast transcription termination signal, and restriction site for cloning, can be used in the manufacture of said yeast episomal expression vector; nevertheless, in a particular embodiment, the glyceraldehyde-3-phosphate dehydrogenase promoter (pGPD) is used as the yeast-functional promoter; in another particular embodiment, the URA3 gene (URA3) is used as yeast selection gene; in another particular embodiment, the yeast 2 microns (2µ) replication origin is used as the yeast replication origin; in another particular embodiment, the ampicillin resistance gene (Amp) is used as the bacterial selection gene; and in another particular embodiment, the transcription termination signal of the phosphoglycerate kinase (PGKt) is used as the specific yeast transcription termination signal. Thus, in a specific embodiment (Example 1-2), the yeast episomal expression vector comprises (i) the URA3 gene; (ii) the Amp gene for selecting and propagating the vector in $E.$ $coli$; (iii) the yeast 2µ replication origin; (iv) the pGPD; (v) the specific yeast transcription termination signal of PGKt; and (vi) a unique BamHI restriction site that allows cloning of selected genes under the control of the pGPD, and followed by the PGKt sequence. In other embodiment, said yeast expression vector is a yeast integrative expression vector. The term "yeast integrative expression vector" as used herein refers to a vector which is capable of integrating into the yeast genome. In a particular embodiment, said yeast integrative expression vector comprises: (i) a bacterial selection gene; and (ii) an expression cassette inserted in a yeast selection gene, said expression cassette further comprising a yeast-functional promoter, a yeast transcription termination signal and a unique restriction site for cloning the selected gene (TF protein or a fragment thereof having pro-coagulant activity).

Practically any bacterial selection gene, expression cassette inserted in a yeast selection gene, yeast-functional promoter, yeast transcription termination signal, and unique restriction site for cloning the selected gene, can be used in the manufacture of said yeast integrative expression vector; nevertheless, in a particular embodiment, the ampicillin resistance gene (Amp) is used as the bacterial selection gene; in another particular embodiment, the expression cassette pGPD-BamHI-PGKt inserted in the central region of the URA3 gene is used as expression cassette containing a yeast-functional promoter (pGDP), a yeast transcription termination signal (PGKt), and unique restriction site (BamHI) for cloning the selected gene in the central region of the URA3 gene.

Virtually any yeast cell susceptible of being transformed with said yeast expression vector comprising the nucleotide sequence coding for TF protein or a fragment thereof having pro-coagulant activity, operatively linked to a yeast-functional promoter, can be used in the present invention. Transformation of yeast cells with said yeast expression vector can be carried out by conventional means known by the skilled person in the art (Sambrook et al., 2001, Molecular Cloning: A Laboratory Manual).

In a preferred embodiment, said yeast is a non-flocculent yeast (i.e., yeasts cells which when they are dispersed in a fermentation process do not flocculate (aggregate)). Advantageously, said yeast cell is a GRAS yeast cell. Illustrative, non limitative, examples of yeast cells that can be used in the process of the invention are the so-called liquor yeast species (yeasts used for making a liquor) which produce alcohol, carbonic acid gas, baker's yeast, and the like by metabolizing a brewing material liquid. Specifically, preferred ones are selected from *S. cerevisiae*. Examples of such liquor yeast include beer yeast cells, wine yeast cells, and sake yeast cells. In a preferred embodiment of the invention, the yeast cell is a wine yeast cell, such as *S. cerevisiae* T73 ura3-(Example 1).

The term "plant expression vector", as used herein refers to DNA expression constructs, e.g., nucleic acid segments, plasmids, cosmids, phages, viruses or virus particles capable of synthesizing the subject proteins encoded by their respective recombinant genes (i.e., TF protein or a fragment thereof having pro-coagulant activity) carried by the vector in a plant. Alternatively, nucleic acid segments may also be used to create transgenic plant cells, using non-directional or homologous recombination, in which the gene or genes of interest are stably integrated into the plant genome. Normally, the plant expression vector comprises the nucleotide sequence coding for TF or a fragment thereof having pro-coagulant activity operatively linked to a promoter which is functional in plant cells (i.e., a plant-functional promoter). Plant functional promoters that can be sued in the present invention can be selected from the group consisting of corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, petunia chalcone isomerase, bean glycine rich protein 1, Potato patatin, lectin, CaMV 35S, and the S-E9 small subunit RuBP carboxylase promoter. The transformation of plant host systems may be carried out by using conventional methods. A review of the genetic transfer to plants may be seen in the textbook entitled "Ingeniería génetica y transferencia génica", by Marta Izquierdo, Ed. Pirámide (1999), in particular, Chapter 9, "Transferencia génica a plantas", pages 283-316.

Vectors for use with the invention are, for example, vectors capable of autonomous replication and/or expression of nucleic acids to which they are linked in yeast cells. In the present specification, the terms "plasmid" and "vector" are used interchangeably as the plasmid is the most commonly used form of a vector. Moreover, the invention is intended to include such other forms of expression vectors that serve equivalent functions and which become known in the art subsequently hereto. Said yeast expression vector may be a plant episomal expression vector or a plant integrative expression vector, and they can be obtained by conventional techniques known for the skilled person in the art. Practically any plant-functional promoter, plant selection gene, plant replication origin, bacterial selection gene, plant transcription termination signal, and restriction site for cloning, can be used in the manufacture of said plant episomal expression vector.

A large number of particular plant production systems have been developed. These include expressing protein on oil bodies (Rooijen et al., 1995) Plant Physiology 109:1353-61; Liu et al., (1997) Molecular Breeding 3:463-70), through rhizose-cretion (Borisjuk et al., (1999) Nature Biotechnology 17:466-69), in seed (Hood et al., (1997) Molecular Breeding 3:291-306; Hood et al., (1999) In Chemicals via Higher Plant Bioengineering (ed. Shahidi et al.) Plenum Publishing Corp. pp. 127-148; Kusnadi et al., (1997) Biotechnology and Bioengineering 56:473-84; Kusnadi et al., (1998) Biotechnology and Bioengineering 60:44-52; Kusnadi et al., (1998) Biotechnology Progress 14:149-55; Witcher et al., (1998) Molecular Breeding 4:301-12), as epitopes on the surface of a virus (Verch et al., (1998) J. Immunological Methods 220: 69-75; Brennan et al., (1999) J. Virology 73:930-38; Brennan et al., (1999) Microbiology 145:211-20), and by stable expression of proteins in potato tubers (Arakawa et al., (1997) Transgenic Research 6:403-13; Arakawa et al., (1998) Nature Biotechnology 16:292-97; Tacket et al., (1998) Nature Medicine 4:607-09). Recombinant proteins can also be targeted to the seeds, chloroplast or secreted to identify the location that gives the highest level of protein accumulation. Each of these could be adapted to express the tissue factor or fragment in a suitable plant host.

Additional general methods for expressing proteins in plants have been reported. See PCT/US02/23624 to Bascomb, N. et al.; and PCT/US02/17927 to Hall, G. et al. These could be readily adapted to express the tissue factor protein or fragment in, for instance, *Arabadopsis* as well as a variety of other plants.

Further methods for expressing heterologous proteins in monocotyledenous and dicotyledenous plants have been reported. These include approaches that result in stable and constitutive expression of the protein of interest: 1) *Agrobacterium*-mediated gene transfer; 2) direct DNA uptake including methods for direct uptake DNA into protoplasts; 3) DNA uptake induced by brief electric shock of plant cells, 4) DNA injection into plant cells or tissues by particle bombardment, by the use of micropipette systems or by the direct incubation of DNA with germinating pollen; and 5) the use of plant virus as gene vectors. One or a combination of these methods can be used to create plants that express tissue factor and functional fragments thereof.

Gene transfer by means of engineered *Agrobacterium* strains has become routine for most dicotyledonous plants and for some monocotyledonous plants. See e.g., Fraley et al. (1983) Proc. Natl. Acad. Sci. USA 80:4803. Further vectors for use with the invention include those "super-binary" disclosed in U.S. Pat. No. 5,591,616 and EPA 0604662A1, for instance. See also Hood et al. (1984) Biotechnol. 2:702-709; Hood et al. (1986) J. Bacteriol. 168:1283-1290; Komari et al. (1986) J. Bacteriol. 166:88-94; Jin et al. (1987) J. Bacteriol. 169:4417-4425; Komari T. (1989) Plant Science 60:223-229; ATCC Accession No. 37394).

The term "animal expression vector", as used herein refers to DNA expression constructs, e.g., nucleic acid segments, plasmids, cosmids, phages, viruses or virus particles capable of synthesizing the subject proteins encoded by their respective recombinant genes (i.e., TF protein or a fragment thereof having pro-coagulant activity) carried by the vector in an animal cell. Alternatively, nucleic acid segments may also be used to create transgenic animal cells, using non-directional or homologous recombination, in which the gene or genes of interest are stably integrated into the animal genome. Normally, the animal expression vector comprises the nucleotide sequence coding for TF or a fragment thereof having pro-coagulant activity operatively linked to a promoter which is functional in animal cells (i.e., an animal-functional promoter).

In a particular embodiment, the animal cells are insect cells. Examples of insect transfection systems include insect specific virus such as the recombinant Baculoviruses used in the present invention (see examples) an others such as the ones described in the U.S. Pat. No. 6,130,074A.

In those embodiments wherein the cell wherein the TF or the variant thereof is to be expressed is yeast, the yeasts are manipulated using standard techniques for manipulation of yeast and yeast genetics. See, for example, Bacila et al., eds. (1978, Biochemistry and Genetics of Yeast, Academic Press, New York); and Rose and Harrison. (1987, The Yeasts (2.sup.nd ed.) Academic Press, London). Methods of introducing exogenous DNA into yeast hosts are well known in the art. There are a wide variety of methods for transformation of yeast. Spheroplast transformation is taught by Hinnen et al (1978, Proc. Natl. Acad. Sci. USA 75:1919-1933); Beggs, (1978, Nature 275(5676):104-109); and Stinchcomb et al., (EPO Publication No. 45,573; herein incorporated by reference), Electroporation is taught by Becker and Gaurante, (1991, Methods Enzymol. 194:182-187), Lithium acetate is taught by Gietz et al. (2002, Methods Enzymol. 350:87-96) and Mount et al. (1996, Methods Mol. Biol. 53:139-145). For a review of transformation systems of non-Saccharomyces yeasts, see Wang et al. (Crit. Rev Biotechnol. 2001; 21(3): 177-218). For general procedures on yeast genetic engineering, see Barr et al., (1989, Yeast genetic engineering, Butterworths, Boston).

Once the eukaryotic cell is transformed with a TF-expressing vector of choice, the next step consists in growing a culture of recombinant eukaryotic cells which express TF protein or a fragment thereof having pro-coagulant under conditions which allow the expression of said TF protein, or fragment thereof having pro-coagulant activity. In a particular embodiment, said eukaryotic cell is grown in an adequate media wherein said eukaryotic cell can express the desired heterologous product (TF protein or fragment thereof having pro-coagulant activity). Appropriate culture media for growing yeast, plant, insect, fish, mammalian or other eukaryotic cells are well known for those skilled in the art and will be selected according to the type eukaryotic cells to be cultured. Any material for making a fermentation or growing product may be used as long as it is suitable for fermentation or growing caused by the eukaryotic cells employed, and known materials can be used at will. Appropriate nutrients and the like may be added thereto when necessary.

Fermentation or cell culture conditions are not different from known conditions in essence and can be fixed by the skilled person in the art. Growing conditions that should be regulated are the gas composition (oxygen, etc), temperature, pH, etc. The documents U.S. Pat. No. 5,618,676, U.S. Pat. No. 5,854,018, U.S. Pat. No. 5,856,123 and U.S. Pat. No. 5,919,651 described methods and reactive adequate for the expression of recombinant proteins using yeast promoters. In a particular embodiment, fermentation of yeast cells is followed by controlling the evolution of the main parameters throughout the fermentation process and it is stopped when the oxygen pressure ($PO_2$) reaches a stationary state.

In a second step, the first method of the invention comprises recovering of TF-bearing microvesicles from the cells which have been obtained in the step (i).

The term "recovering" as used herein refers to the act of separating the TF-bearing microvesicles from intact or lysed cells as well as from other cell components such as DNA, proteins, etc and thus obtaining a partially or totally purified preparation of TF-bearing microvesicles. In a preferred embodiment the purity of the fraction recovered is of at least 50%, at least 60%, at least 70%, at least 80%, at least 90%, at least 99% and 100%.

The recovery requires the lysis of the cells in the absence of detergents or, when detergents are used, using concentrations of said detergents below the critical micellar concentration (CMC). In the case that the cells are obtained form a whole organism like a transgenic plant or a transgenic animal, the recovering may include a step of reducing the tissue to a cell suspension using mechanical or enzymatic methods.

The cell suspension or the cells from the cell culture, in the case that the TF-bearing microvesicles are recovered from cell cultures, can be pelleted by conventional methods, such as by centrifugation, and re-suspended in a suitable lysis buffer prior to subjecting said product to homogenization.

Plant and fungi cells have a cellulose and chitin walls. Thus, prior to the homogenization, an extra step cells may be required in order to remove the cell wall. This step may be performed using mechanical (e.g., by use of a morter and pestle, french press, blender and the like) or enzymatic methods (e.g. using cellulase, quitinase, etc) in the presence of a pharmaceutically acceptable solution o lysis buffer (water, phosphate-buffered saline (PBS), etc.).

Moreover, prior to the homogenization, the debris can be removed by filtration or gentle centrifugation, typically about 1,000.times.g for less than about 30 minutes, preferably between from about 5 to about 20 minutes.

The methods for recovering the TF-bearing microvesicles from the cells obtained in the first step of the first method of the invention may vary depending of the eukaryotic cells used and include without limitation, centrifugation, gel filtration chromatography, tangential flow filtration or a combination thereof.

In a preferred embodiment, the cells are lysed by mechanical means and the nuclei, unbroken cells and debris are removed by low-speed centrifugation, providing a post-nuclear supernatant (PNS) Thus, in a preferred embodiment, the lipid microvesicle preparation is a post-nuclear supernatant.

In the particular case when yeast cells are used as host cells for the preparation of TF-bearing microvesicles, yeasts cells can be homogenized by conventional methods such as high pressure in a homogenizer to render a fermentation homogenate. The fermentation homogenate is then subjected to separation by conventional methods, such as by centrifugation, to render a pellet and a clarified yeast extract (CYE) containing said TF-bearing yeast derived microvesicles having pro-coagulant activity (i.e., the TF-bearing yeast derived microvesicle of the invention) which can be collected separately.

The presence of TF protein or a fragment thereof having pro-coagulant activity can be determined by conventional methods, such as, by Western-blot analysis by using a specific anti-TF protein monoclonal antibody (mAb). Further, the pro-coagulant activity of the CYE can be determined by any conventional assay, such as by any of the coagulation assays mentioned in Example 4, e.g., typically by an in vitro coagulation assay in plasma or in non-anticoagulated whole blood, etc.

Further examination of CYE samples by immunoelectron microscopy with a labelled anti-TF mAb may be applied in order to identify the presence of TF in yeast- or in other eukaryotic-derived microvesicles. Said microvesicles, which comprise TF protein or a fragment thereof having pro-coagulant activity, have also pro-coagulant activity and correspond to the TF-bearing eukaryotic derived microvesicles of the invention.

Optionally, if desired, said TF-bearing eukaryotic cell derived microvesicles (such a yeast derived microvesicle) having pro-coagulant activity may be concentrated, isolated or purified by conventional methods known by the skilled person in the art. By way of illustration, affinity chromatography purification of proteins containing a peptide tag (e.g., a His-tag, etc.), either at the C- or N-terminus, is a well standardized method used to obtain highly purified preparations of a large number of proteins. As any chromatographic method, said method can be easily scaled-up. Alternative purification procedures such as immunoaffinity chromatography could be performed, although it would require the availability of well standardized stocks of specific anti-TF mono or polyclonal antibodies, especially for a scaled-up production.

Thus, the isolation and purification method will depend, among other things, on the nature of the TF protein or fragment thereof having pro-coagulant activity, i.e., if it is a fusion protein having a tag for binding to one or more ligands of an affinity matrix such as a chromatography support or bead with high affinity (e.g., a His-tag, etc.), or an epitope capable of being recognized by an antibody, such as c-myc-tag (recognized by an anti-c-myc antibody), etc.

In a preferred embodiment, the histidine-tagged TF-bearing yeast derived microvesicles of the invention are obtained from a clarified yeast extract (CYE) according to the process previously disclosed. Typically, the CYE is filtered (e.g., through a 0.2 µm pore size filter by tangential flow filtration) before being loaded over an appropriate affinity column (e.g., HiTrap-affinity column); then, after applying the sample, the flow-through is recovered (unbound material), and the column is subjected to several washes and, after the last wash, the (TF-His-tag protein)-bearing yeast derived microvesicles are eluted by adding to the column an appropriate buffer (e.g., a buffer containing imidazol) and the elution fractions are collected and dialyzed to render isolated or purified (TF-his-tag protein)-bearing yeast derived lipid microvesicles.

Also, in another embodiment, the TF-bearing microvesicles of the invention can be purified by an ÄKTA prime equipment. The ÄKTA prime is an automated liquid chromatographic system from General Electric Healthcare that can be used for the development of standard purification protocols using size exclusion chromatography columns that could be easily scaled-up for large productions. In another embodiment, tangential flow filtration or High-performance tangential flow filtration (HPTFF) can be used.

In a particular embodiment, the TF-bearing microvesicles are recovered using a combination of one or more steps of tangential flow filtrations and/or one or more steps of size exclusion chromatography.

In a particular embodiment, the TF-bearing yeast microvesicles are recovered using one step of tangential flow filtration followed by one size exclusion chromatography and followed by another tangential flow filtration. In a preferred embodiment, the pore size of the first tangential flow filtration is bigger than the pore size of the second (and subsequent) tangential flow filtrations. In a more preferred embodiment, the size pore of the first tangential flow filtration is form 0.5 to 0.1 µm and the pore size from the second tangential flow filtration is from 0.2 µm.

In a third step, the first method of the invention comprises contacting of the microvesicles obtained in step (ii) with a negatively charged phospholipid under conditions adequate for the incorporation of said phospholipid into said microvesicles.

The term "phospholipid" as used herein refers to a lipid that contains one or more phosphate groups. Phospholipids are amphipathic in nature; that is, each molecule consists of a hydrophilic (water-loving) portion and a hydrophobic (water-hating) portion. Herein, the term "phospholipid" includes pharmaceutically acceptable salts and ester derivatives of such compounds.

Phospholipids can be classified according to the type of alcohol in phosphoglycerides (or glycerophospholipids) when they carry a glycerol backbone and sphingolipids wherein the lipids contain sphingosine. Both classes are present in the biological membrane. Phosphoglycerides are the most abundant class of phospholipids found in nature and include, without limitation, phosphatidylcholine (lecithin), phosphatidylethanolamine, phosphatidylserine, phosphatidylinositol, phosphatidylglycerol, and cardiolipin. The structural diversity within each type of phosphoglyceride is due to the variability of the chain length and degree of saturation of the fatty acid ester groups.

Sphingomyelin is the major sphingosine-containing phospholipid. Its general structure consists of a fatty acid attached to sphingosine by an amide linkage.

The term "negatively charged phospholipid" or "NCP" refers to phospholipids that carry a net negative charge at physiological pH levels, i.e. over the range of about pH 7.3 to 7.5. Examples of negatively charged phospholipids that can be used in the present invention include phosphatidylserine (PS), dipalmitoyl and distearoyl phosphatidic acid (DPPA, DSPA), dipalmitoyl and distearoyl phosphatidylserine (DPPS, DSPS), dipalmitoyl, distearoyl phosphatidylglycerol (DPPG, DSPG), phosphatidylglycerol, phosphatidylinositol, cardiolipin, sphingolipids (ceramides-1-phosphate; glycosilated phosphatidyl etanolamine; sulfatides (hydroxilated or not); gangliosides), phosphatidylinositolphosphates and phosphatidic acid.

In a preferred embodiment, the negatively charged phospholipid is phosphatidylserine (PS), which is phospholipid formed by esterification between the phosphate group in the phosphatidic acid molecule and the hydroxyl group in serine and having the structure depicted in formula

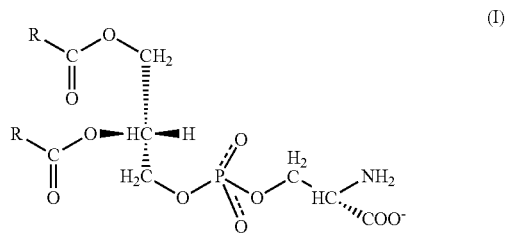

wherein the R is a fatty acid. The term "fatty acid", as used herein, refers to long chain aliphatic acids (alkanoic acids) of varying chain lengths, from about $C_{12}$ to $C_{22}$, containing none, one or more than one insaturation. Preferably, the fatty acid is selected from the group of stearic acid (18:0 or octadecanoic acid), oleic acid (18:1 cis-9 or (9Z)-octadec-9-enoic acid), palmitic acid (16:0 or hexadecanoic acid), linoeic acid (18:2(ω-6) or cis, cis-9,12-octadecadienoic acid), arachidonic acid (20:4 (ω-6) or all-cis-5,8,11,14-eicosatetraenoic acid), docosohexanoic acid (22:6 (n-3 or (4Z,7Z,10Z,13Z, 16Z,19Z)-docosa-4,7,10,13,16,19-hexaenoic acid).

Negatively charged phospholipids for use in the present invention may be purified or isolated or substantially pure. A compound is "substantially pure" when it is separated from the components that naturally accompany it. Typically, a compound is substantially pure when it is at least 60%, more generally 75% or over 90%, by weight, of the total material in a sample. A substantially pure phospholipid can be obtained, for example, by extraction from a natural source or by chemical synthesis. Thus, for example, a phospholipid that is chemically synthesised will generally be substantially free from its naturally associated components. Purity can be measured using any appropriate method such as column chromatography, gel electrophoresis, HPLC, etc. However, it is not essential for a negatively charged phospholipid to be purified prior to use in the present invention, provided that the phospholipid is not associated with components that interfere substantially with its utility. The skilled person will appreciate that a natural source or partially-purified source of a negatively charged phospholipid may be used in the invention, and that the negatively charged phospholipid component may constitute a small percentage (for example 10-20%, but preferably at least 30%, 40%, 50% or more) of the total material obtained from such a source.

The process of contacting the microvesicles obtained in the second step (ii) of the first method of the invention with a negative charged phospholipid is made under conditions adequate for incorporation of the negative charged phospholipid within the lipid microvesicle. Variables which can be optimized during the incubation step include temperature, pH, adequate buffers, humidity, components concentration, solutions, washing steps, etc; These variables may be adjusted as necessary to obtain an optimal microvesicle/phospholipid ratio.

As described before, the vesicle preparation obtained in step (i) of the first method of the invention is compose of membrane lipids as well as of proteins which include the tissue factor or variant thereof expressed in the host cell as well as membrane-associated proteins which appear endogenously in the host. However, for the purposes of quantifying the microvesicle yield, it is typically more convenient to express the microvesicle concentration as micrograms of protein per volume unit. Protein concentration in the microvesicle sample can be determined using standard protein quantification technologies, such as the Bradford assay, the BCA assay, the Biuret assay and the like.

Once the protein concentration in the microvesicles has been determined, the contacting step can be carried out using any suitable ratio of phospholipid to microvesicle. The skilled person will appreciate that the ratio of phospholipid to vesicles in the contacting step can be varied according to the needs in order to achieve a vesicle preparation showing the best properties. Preferably, the adequate end concentration of negatively charged phospholipid can be calculated using a "saturation curve assay" by mixing the particular negatively charged phospholipid used and increasing concentrations of the microvesicles obtained in step (ii) and determining the coagulation times of the resulting vesicles until an optimal concentration of both components is determined. While this concentration ratio usually corresponds to the concentration ratio that results in the substantially no free negatively charged phospholipid (i.e not incorporated to the microvesicles), the invention also contemplates ratios of both components which lead to an excess of unincorporated phospholipid which may be removed by conventional methods. The person skilled in the art would also understand that the negatively charged phospholipid would be included in the lipid bi-layer of the microvesicle obtained in step (ii) at different rates depending on the nature of the negatively charged phospholipid and the nature of the microvesicle obtained in step (ii) (i.e yeast derived microvesicle, insect derived microvesicle, etc).

In a preferred embodiment, the contacting step is carried out using a protein concentration of about 0.1 to 1000 μg/ml, 1 to 100 μg/ml, 10-90 μg/ml, 20-80 μg/ml, 30-70 μg/ml, 40-60 μg/ml, 45-55 μg/ml or μg/ml. The phospholipid concentration in the contacting step is preferably 0.001 mM-1 mM, 0.005 mM-0.5 mM, 0.1 mM-0.4 mM, 0.2 mM-0.3 mM.

In a preferred embodiment, the contacting step is carried out using a protein/phospholipid ratio of about X μg of protein to about 0.005-1 μmol of phospholipid, wherein X is about 5, 10, 30, 40, 50, 60, 70, 80, 90 or 100. In a still more preferred embodiment, the contacting step is carried out using 0.05 μmol of phospholipid for a vesicle preparation having 50 or less than 50 μg of protein or a 1 mmol of phospholipid for a vesicle preparation having at least 50 μg of protein.

While the contacting step is usually carried out under conditions adequate for incorporation of most of the phospholipid into the vesicles without leaving any substantial phospholipid excess, this may not be necessarily so, in which case an additional step may be carried out wherein the excess of negatively charged phospholipid is removed from the preparation of phospholipid-enriched microvesicles obtained in step (ii). Different methods for removing the excess are known from the person skilled in the art such as additional washing steps, layer separation, centrifugation, chromatography, etc.

The excess phospholipid can be removed from the phospholipid-enriched microvesicles by a number of methods resulting in a stable TF-bearing microvesicle composition having tissue factor associated with and inserted through the lipid bilayer. Suitable methods of removal of detergent include dialysis, tangential flow diafiltration, cross flow hollow fiber filtration, treatment with hydrophobic chromatography resin, and simple dilution.

Second Method of the Invention

In a second aspect, the invention relates to a method for the preparation of a TF-bearing microvesicle, or second microvesicle of the invention, having pro-coagulant activity which comprises the steps of
  (i) providing a lipid microvesicle obtained from an eukaryotic cell,
  (ii) contacting a TF protein or a variant thereof having pro-coagulant activity with a lipid microvesicle as defined in (i) under conditions adequate for the incorporation of said TF protein or variant thereof into said microvesicles and
  (iii) contacting the vesicles obtained in step (ii) with a negatively charged phospholipid under conditions adequate for the incorporation of said phospholipids into said vesicle,
wherein steps (ii) and (iii) can be carried out in any order.

The terms "TF", "TF variant having pro-coagulant activity", and "negatively charged phospholipid" have been described in detail in the context of the first method of the invention and are equally applicable to the second method of the invention.

In a first step of the second method of the invention, lipid microvesicles obtained from an eukaryotic cell are provided. The lipid microvesicles used in the second method of the invention can be microvesicles derived from any type of eukaryotic cell as described in the first method of the invention using the methods described in the first method of the invention and include, without limitation, vesicles isolated from yeast cells, mammalian cells, insect cells, fish cells and plant cells. As described in the context of the first method of the invention, the lipid microvesicles are typically obtained in the absence of detergents or in the presence of detergents wherein these are found at concentrations below the critical micellar concentration.

In a second step, the lipid microvesicles are contacted with a TF protein or a variant thereof having pro-coagulant activity under conditions adequate for the incorporation of said TF protein or variant thereof into said microvesicles. The microvesicles obtained as described above are then contacted with a TF protein which can be obtained from tissue extracts or provided as (partially) purified recombinant protein. The preparation of extracts and purification of TF can be carried out from several tissues such as cerebral, placental and lung tissue, and from different animals such as sheep, cows, rabbits, dogs, and humans. The preparation of extracts and purification of TF protein can be perform as described, without limitation, in U.S. Pat. No. 5,622,931. The TF used can be a recombinant TF (rTF) that can be obtained from any cellular expression system, preferably from eukaryotic cells. The rTF used in carrying out this invention may further be part of a fusion protein, as it was described previously. The eukaryotic cells and methods for heterologous expression of proteins that can be used in the second method of the invention have been described previously.

The second method of the invention may further comprise the step of removing the TF excess from step (ii). Methods for removing the TF excess from step (ii) are essentially the same as those mentioned in the context of the first method of the invention and include gel filtration chromatography, differential centrifugation, density gradient centrifugation and the like.

In a third step, the second method of the invention comprises contacting of the vesicles obtained in step (ii) with a negative charged phospholipid under adequate conditions for the incorporation of the phospholipids into said vesicles.

The negative charged phospholipid that can be used in the present intention as well as the conditions which are adequate for the incorporation of the phospholipids into said vesicles have been described in the detail in the first method of the invention. In a preferred embodiment, the negative charged phospholipid used is phosphatidylserine.

The expression "conditions adequate for incorporation of the phospholipids in the vesicles" is to be understood herein as any condition that allows the phospholipids to move freely and integrate in the microvesicles. While not particularly limiting, the conditions usually involve a temperature of about 4 C to 90 C, 10 C to 80 C, 15 C to 70 C, 20 C to 60 C, 25 C to 50 C, 30 C to 40 C or room temperature, a pH of 2-12, 3-11, 4-10, 5-9, 6-8 or 7 and physiological salt concentrations.

In a preferred embodiment, the contacting step is carried out using a vesicle preparation having protein concentration of about 0.1 to 1000 µg/ml, 1 to 100 µg/ml, 10-90 µg/ml, 20-80 µg/ml, 30-70 µg/ml, 40-60 µg/ml, 45-55 µg/ml or µg/ml. The phospholipid concentration in the contacting step is preferably 0.001 mM-1 mM, 0.005 mM-0.5 mM, 0.1 mM-0.4 mM, 0.2 mM-0.3 mM.

In a preferred embodiment, the contacting step is carried out using a protein/phospholipid ratio of about X to about 0.005-1 µmol of phospholipid, wherein X is about 5, 10, 30, 40, 50, 60, 70, 80, 90 or 100 µg of protein. In a still more preferred embodiment, the contacting step is carried out using 0.05 µmol of phospholipid for a vesicle preparation having 50 or less than 50 µg of protein or a 1 µmol of phospholipid for a vesicle preparation having at least 50 µg of protein.

The second method of the invention can further comprise the step of removing the PS excess from step (iii). Methods for removing the PS excess from step (iii) are essentially the same as those mentioned in the context of the first method of the invention and include gel filtration chromatography, differential centrifugation, density gradient centrifugation and the like.

The second method of the invention can be also be performed carrying steps (ii) and (iii) in reverse order, i.e. by first contacting a vesicle with a negatively charged phospholipid followed by contacting the vesicles obtained in the first step with TF. Thus, in another aspect, the invention comprises a first step wherein a lipid microvesicle is contacted with a negative charged phospholipid under appropriated conditions for the incorporation of the phospholipids into said vesicles and a second step wherein in the vesicles obtained in the first step are contacted with a recombinant TF or a variant thereof having pro-coagulant activity under conditions adequate for the incorporation of the recombinant TF into the microvesicles.

Conditions adequate for performing the first and second steps are essentially as described above.

Microvesicles of the Invention

Both the first and second methods of the invention result in TF-bearing microvesicles which show improved pro-coagulant properties and increased stability in comparison with microvesicles which have not been contacted with negatively-charged phospholipids. Thus, in another aspect, the invention relates to a microvesicle which has been prepared using the first or the second method of the invention.

The term "microvesicle" has been described in detail above and refers essentially to a closed compartment comprising essentially a lipid monolayer or a lipid bilayer. The microvesicles may show a diameter which varies within a broad range. Typically, said size is equal to or lower than 10 µm, typically equal to or lower than 0.5 µm. In a particular embodiment, the size of the TF-bearing yeast derived microvesicles of the invention range from 10 to 0.01 µm. Since the microvesicles obtained according to the methods of the invention derive from eukaryotic, their protein and lipid composition will reflect that of the membranes of the organism from wherein it derives.

In the particular case when the microvesicles derive from yeast cells, they usually contain yeast-specific phospholipids such as ergosterol and cardiolipin.

When the microvesicles are derived from plant cells, these contain plant cell membrane-specific lipids such as phytosterol, stanols, stanolesters, tocopherols, d-alpha tocopherols, d, l-alpha tocopherols, tocotrienols, phytosterol or triterpene comprising a beta-sitosterol, a campesterol, a stigmasterol, a stigmastanol, a beta-sitostanol, a sitostanol, a desmosterol, a chalinasterol, a poriferasterol, a clionasterol or a brassicasterol.

When the microvesicles are derived from animal cells, these contain animal cell membrane-specific lipids such as cholesterol or typical mammal membrane lipid composition.

When the microvesicles are derived from insect cells, these contain insect cell membrane-specific lipids or typical insect membrane lipid composition such as high amounts of diacylglycerol. (Insect Lipids: Chemistry, Biochemistry, and Biology Book by David W. Stanley-Samuelson, Dennis R. Nelson; University of Nebraska Press, 1993).

Although it is preferred that the microvesicles of the invention are free from other particulate matter, the procoagulant effect is observed within a wide range of purity of the microvesicles. Thus, the microvesicles of the invention may be provided in a preparation comprising, with respect to non-microvesicle particulate matter, at least 10%, at least 20%, at least 30%, at least 40%, at least 50%, at least 60%, at least 70%, at least 80% or at least 90% microvesicles.

Lyophilized Compositions of the Invention

As those skilled in the art will recognize, any of the microvesicle compositions of the invention may be lyophilized for storage, and reconstituted, for example, with an aqueous medium (such as sterile water, phosphate buffered solution, or aqueous saline solution), with the aid of vigorous agitation.

The term "lyophilization", "freeze-drying" or the grammatical equivalent variants thereof, refer to a dehydration process typically used to preserve a perishable material or make the material more convenient for transport which works by freezing the material and then reducing the surrounding pressure and adding enough heat to allow the frozen water in the material to sublime directly from the solid phase to gas.

Different lyophilization and freezing procedures that may be used are known by a person skilled in the art. Lyophilization can be carried out using standard equipment such as rotary evaporators, manifold freeze-dryers and tray freeze-dryers. In a particular embodiment, the pharmaceutical compositions of the invention may be frozen on dry ice, then lyophilized using a cycle beginning at −40° C. and ending at room temperature, over a 48 hour period. The resulting reagent may be reconstituted to working concentration with the addition of 0.1M Tris, pH 7.5, 150 mM trehalose to yield a solution containing the first or second vesicles of the invention at approximately 10-250 µg/ml.

To prevent agglutination or fusion of the lipids and/or vesicles as a result of lyophilization, it may be useful to include cryoprotectans which prevent such fusion or agglutination from occurring. The term "cryoprotectant" refers to an agent that protects a lipid particle subjected to dehydration-rehydration, freeze-thawing, or lyophilization-rehydration from vesicle fusion and/or leakage of vesicle contents and include, without limitation, sorbitol, mannitol, sodium chloride, glucose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosures of which are hereby incorporated herein by reference in their entirety. Lyophilized preparations generally have the advantage of greater shelf life.

First Pharmaceutical Compositions of the Invention

In another aspect, the invention relates to a pharmaceutical composition of the invention which comprises the vesicles obtained according to the first and second method of the invention, either in solution/suspension or in lyophilized form and a pharmaceutically active vehicle. Said pharmaceutical composition is then formulated in a pharmaceutical administration form suitable for its administration to a subject.

The pharmaceutical compositions of the invention comprise microvesicles of the invention comprising human TF protein or any of the variants thereof having pro-coagulant activity and which have been described in detailed above, including mature human TF, truncated human TF, glycosylation variants of TF, tagged TF and variants carrying more than one of the above modifications such as the mature TF carrying an hexahistidine tag at the C-terminus and a N124A mutation.

The term "pharmaceutically acceptable vehicle", as used herein, refers to any substance suitable for delivering a therapeutic composition useful in the method of the present invention to a suitable in vivo or ex vivo site without causing undesirable adverse effects as toxicity, irritation, allergic reaction or other problem or complication with a reasonable risk of occurrence. Practically, any vehicle which does not adversely affect the first or second microvesicles of the invention can be used in said compositions of the invention. In an embodiment, said vehicle is a substantially liquid medium, such as the medium surrounding the TF-bearing microvesicles of the invention obtained by working the process of the invention. Therefore, in a particular embodiment, the first composition of the invention comprises the clarified eukaryotic extract obtained in the working of the process of the invention wherein the negatively-charged phospholipid has been added.

Information about carriers and excipients, as well as about said administration forms suitable for the administration of said product of the invention, can be found in galenic pharmacy treatises. A review of the different pharmaceutical administration forms of drugs in general, and of their preparation processes, can be found in the book entitled "Tratado de Farmacia Galénica", by C. Faulí i Trillo, 1st Edition, 1993, Luzán 5, S.A. of Ediciones.

In a particular embodiment the microvesicles obtained according to the first and second methods of the invention can formulated together.

In a particular embodiment the pharmaceutical composition comprising a TF-bearing microvesicle of the invention can be formulated together with a coagulation promoter.

In the present invention "coagulation promoter" can be considered as any agent that promotes the process by which blood forms clots.

Agents useful as coagulation promoters are adsorbent chemicals such as zeolin; thrombin; components of the clotting cascade such as coagulation Factors II, VII, VIII, IX, X, XI, XII, XIII etc; cofactors such as calcium, vitamin K; and the like. In a preferred embodiment, the coagulation promoter used is selected from the group of factor VII (as precursor or as active form), factor X (as precursor or as active form) and combinations thereof.

Although it is preferred that the pharmaceutical compositions of the invention comprise purified microvesicles, it is also possible that the composition comprises substantially purified microvesicles. The microvesicles can be purified by any of the methods mentioned above in order to yield a preparation comprising, with respect to non-microvesicle particulate matter, at least 10%, at least 20%, at least 30%, at least 40%, at least 50%, at least 60%, at least 70%, at least 80% or at least 90% microvesicles.

The pharmaceutical compositions of the invention comprise a therapeutically effective amount of the TF-bearing microvesicles. Said amount may vary within a wide range depending on the dosage, route of administration and the like. Typically, the pharmaceutical compositions of the invention may comprise between about 10 µg of active microvesicle of the invention/ml and 300 µg of active microvesicle of the invention/ml, preferably between 20 µg of active protein/ml and 200 µg of active protein/ml, and even more preferably between about 50 µg of active microvesicle of the invention/ml and 100 µg of active microvesicle of the invention/ml.

The dose to be administered to the subject may vary within a very broad range, for example, between about 1.0 pg of active microvesicle of the invention/ml and 1.0 mg of active microvesicle of the invention/ml, preferably between 0.05 µg of active microvesicle of the invention/ml and 100 µg of active microvesicle of the invention/ml, and even more preferably between about 0.1 µg of active microvesicle of the invention/ml and 50 µg of active microvesicle of the invention/ml. The first or second microvesicles of the invention dose to be administered will depend on several factors, including among them the features of the TF protein or fragment thereof having pro-coagulant activity used, such as for example, its activity and biological half life, concentration of the TF protein or fragment thereof having pro-coagulant activity in the formulation, the clinical condition of the subject or patient, the hemorrhagic disorder to be treated, etc. For this reason the doses mentioned herein must be considered only as guides for a person skilled in the art, and this person must adjust the doses according to the previously mentioned variables. Nevertheless, the pharmaceutical composition of the invention can be administered one or more times a day for preventive or therapeutic purposes.

Wherein the TF-bearing microvesicles are lyophilized, they may be resuspended in solvent for re-assembly prior to administration to an animal. When delivered lyophilized, the microvesicles spontaneously reform once the composition is exposed to the hydrophilic environment inside the body of an animal.

Second Pharmaceutical Compositions of the Invention

The authors of the present invention have observed that the procoagulant activity of microvesicles comprising TF obtained from a eukaryotic cell can be synergistically enhanced by combining the vesicles with a coagulation promoter.

Thus, in another aspect, the invention relates to a pharmaceutical composition which comprises
  (i) a microvesicle obtained by a method comprising the steps of
     a) expressing TF or a variant thereof having pro-coagulant activity in an eukaryotic cell and
     b) recovering TF-bearing microvesicles from the cells of step (i),
  (ii) at least an agent that promotes coagulation and
  (iii) a pharmaceutically effective vehicle The terms "microvesicle", "TF", "functionally equivalent variant of TF", "eukaryotic cell", "agent that promotes coagulation" and "pharmaceutically effective vehicle" have been described in detail above and are used essentially in the same manner in respect of the second pharmaceutical composition of the invention.

The first component of the second pharmaceutical compositions of the invention is a microvesicle obtained by a method comprising the steps of
  a) expressing TF or a functionally equivalent variant thereof having pro-coagulant activity in an eukaryotic cell and
  b) recovering TF-bearing microvesicles from the cells of step (i), In a preferred embodiment, the eukaryotic cell is a yeast cell, in which case the microvesicles yeast membrane derived from the yeast cells used in the production of the TF-bearing yeast derived microvesicle of the invention and which comprise the lipids which usually form part of the yeast membranes and proteins which are typically found embedded in the yeast membranes. Typically a membrane is composed of two oriented lipid layers (i.e., a lipid bilayer) in which proteins can be embedded. A lipid bilayer, which is the basic structure of the membranes of a cell, is usually formed by amphipathic molecules (e.g. phospholipids, fatty acids etc.) in an aqueous environment, each molecule being oriented with the hydrophilic group on the outside of the layer and the hydrophobic group to the interior of the layer. The microvesicles derive from yeast cells membranes or fragments thereof, such as, for example, yeast cells plasma membranes or fragments thereof. In another particular embodiment, said yeast derived microvesicle derives from intracellular yeast cells organelles membranes, or fragments thereof, such as nucleus, Golgi apparatus, Endoplasmic reticulum, etc.

Said yeast derived microvesicles will proceed, in general, from the yeast cells used in the production thereof (e.g., after subjecting the yeast fermentation product to an homogenization treatment as shown in the process disclosed in Example 1). Practically any yeast cell can be used for producing said yeast derived microvesicles, advantageously non-flocculent yeast cells, and, preferably, a yeast cell classified as a "Generally Regarded as Safe" (or GRAS) yeast cell by the Federal Drug Administration (FDA) for human consumption, since said GRAS approved substances do not require pre-market approval by the FDA because they are substantially innocuous for animals including human beings. Illustrative, non limitative, examples of yeast cells that can be used in the process for producing the TF-bearing yeast derived microvesicle of the invention are the so-called liquor yeast species which produce alcohol, carbonic acid gas, Baker's yeast, and the like by metabolizing a brewing material liquid. Specifically, preferred yeast cells include yeast cells from *Saccharomyces* sp., etc., for example, *S. cerevisiae* strain T73 ura3-, a derivative of *S. cerevisiae* T73 strain, a strain widely used in wine production (Example 1) or *Pichia* sp.

Adequate method for producing the TF or the functionally equivalent variant thereof as well as for recovering the microvesicles from the eukaryotic cells have been described in detail in the context of the first method of the invention and are equally applicable to the method for obtaining the microvesicles forming part of the second pharmaceutical compositions of the invention.

The term "TF" is essentially as described above and includes both natural TF from any species as well as functionally equivalent variants thereof and which have been described in detailed above, including mature human TF, truncated human TF, glycosylation variants of TF, tagged TF and variants carrying more than one of the above modifications such as the mature TF carrying an hexahistidine tag at the C-terminus and a N124A mutation. In a preferred embodiment, the TF is a mature TF protein. In a still more preferred embodiment, the TF is human mature TF protein. In another preferred embodiment, the TF is mature human TF which carries the N124A mutation and/or carries an hexahistidine tag at the C terminus.

Said pharmaceutical composition is then formulated in a pharmaceutical administration form suitable for its administration to a subject.

Practically, any vehicle which does not adversely affect the first or second microvesicles of the invention can be used in said compositions of the invention. In an embodiment, said vehicle is a substantially liquid medium, such as the medium surrounding the TF-bearing microvesicles of the invention obtained by working the process of the invention. Therefore, in a particular embodiment, the first composition of the invention comprises the clarified eukaryotic extract obtained in the working of the process of the invention wherein the negatively-charged phospholipid has been added.

Information about carriers and excipients, as well as about said administration forms suitable for the administration of said product of the invention, can be found in galenic pharmacy treatises. A review of the different pharmaceutical administration forms of drugs in general, and of their preparation processes, can be found in the book entitled "Tratado de Farmacia Galénica" ("Galenic Pharmacy Treatise"), by C. Faulí i Trillo, 1st Edition, 1993, Luzán 5, S.A. of Ediciones.

Although it is preferred that the pharmaceutical compositions of the invention comprise purified microvesicles, it is also possible that the composition comprises substantially purified microvesicles. The microvesicles can be purified by any of the methods mentioned above in order to yield a preparation comprising, with respect to non-microvesicle particulate matter, at least 10%, at least 20%, at least 30%, at least 40%, at least 50%, at least 60%, at least 70%, at least 80% or at least 90% microvesicles.

The second pharmaceutical compositions of the invention comprise a therapeutically effective amount of the TF-bearing microvesicles. Said amount may vary within a wide range depending on the dosage, route of administration and the like. Typically, the pharmaceutical compositions of the invention may comprise between about 10 µg of active microvesicle of the invention/ml and 300 µg of active microvesicle of the invention/ml, preferably between 20 µg of active protein/ml and 200 µg of active protein/ml, and even more preferably between about 50 µg of active microvesicle of the invention/ml and 100 µg of active microvesicle of the invention/ml.

The dose to be administered to the subject may vary within a very broad range, for example, between about 1.0 pg of active microvesicle of the invention/ml and 1.0 mg of active microvesicle of the invention/ml, preferably between 0.05 µg of active microvesicle of the invention/ml and 100 µg of active microvesicle of the invention/ml, and even more preferably between about 0.1 µg of active microvesicle of the invention/ml and 50 µg of active microvesicle of the invention/ml. The first or second microvesicles of the invention dose to be administered will depend on several factors, including among them the features of the TF protein or fragment thereof having pro-coagulant activity used, such as for example, its activity and biological half life, concentration of the TF protein or fragment thereof having pro-coagulant activity in the formulation, the clinical condition of the subject or patient, the hemorrhagic disorder to be treated, etc. For this reason the doses mentioned herein must be considered only as guides for a person skilled in the art, and this person must adjust the doses according to the previously mentioned variables. Nevertheless, the pharmaceutical composition of the invention can be administered one or more times a day for preventive or therapeutic purposes.

The second pharmaceutical compositions of the invention may be provided in lyophilized form wherein one or more components have been lyophilized. The skilled person will appreciate that the compositions be provided in different forms such as:
  Lyophilised microvesicles and coagulation promoter in suspension,
  Microvesicles in suspension and lyophilised coagulation promoter,
  Lyophilised microvesicles and lyophilised coagulation promoter Wherein both microvesicles and coagulation promoter are provided in lyophilized form, both components can be combined in a single preparation or may be provided in separate containers. Wherein the TF-bearing microvesicles are lyophilized, they may be resuspended in solvent for re-assembly prior to administration to an animal. When delivered lyophilized, the microvesicles spontaneously reform once the composition is exposed to the hydrophilic environment inside the body of an animal. Similarly, wherein the coagulation promoter is lyophilized, it may be resuspended in solvent for re-assembly prior to administration to an animal. When delivered lyophilized, the coagulation promoter is reconstituted when exposed to the hydrophilic environment inside the body of an animal.

Therapeutical Uses of the Invention

Blood Clotting-Related Uses

Different assays have shown that the microvesicles of the invention that comprise a TF-bearing microvesicle having been treated with a negatively charged phospholipid have an enhanced pro-coagulant activity and increased stability. Example 2 shows in vitro assays demonstrating that the microvesicles of the invention cause fibrin clot formation and blood coagulation in both healthy and patient conditions including plasma and blood from healthy patients, plasma deficient in FVIII, FIX or FXI (coagulation assays in plasma); blood from patients showing an acquired platelet deficiency (coagulation assays in Thrombocytopenic blood), plasma deficient in FXI in the presence of an anti-FVII antibody (coagulation assays in plasma) as well as blood from haemophilic, von Willebrand and warfarinized patients. These results clearly show that TF-bearing yeast derived microvesicles of the invention are pro-coagulant or antihemorrhagic agents useful for topical treatment of hemorrhages in a subject.

Thus, in another aspect, the microvesicles of the invention and the pharmaceutical compositions of the invention can be used as a medicament, namely, as a pro-coagulant agent, or as an antihemorrhagic agent, particularly, as an antihemorrhagic agent for topical application, in the treatment of hemorrhages in a subject. Therefore, in another aspect, the invention relates to the first or second microvesicle of the invention for use as a medicament. In further aspects, the invention relates to a method for the treatment of hemorrhages in a subject which comprises the administration of the microvesicles or compositions of the invention to said subject, to the use of the microvesicles or compositions of the invention for the manufacture of a medicament for the treatment of hemorrhages in a subject as well as a microvesicle or composition of the invention for use in the treatment of hemorrhages.

The microvesicles of the invention can be directly used topically for treating the hemorrhage in a subject, i.e., without combining with a pharmaceutically acceptable vehicle, since these microvesicles are substantially innocuous for a subject. However, it is generally preferred that the microvesicles of the invention be formulated in a pharmaceutical administration form suitable for its administration, preferably, for its topical administration for topical (local) treatment of hemorrhaging.

Then, the microvesicles of the invention can be formulated in a pharmaceutical administration form, preferably a pharmaceutical administration form suitable for its topical administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in galenic pharmacy treatises. A review of the different pharmaceutical administration forms of drugs in general, and of their preparation processes, can be found in the book entitled "Tratado de Farmacia Galénica" ("Galenic Pharmacy Treatise"), by C. Fauli i Trillo, 1st Edition, 1993, Luzán 5, S.A. of Ediciones.

Although different pharmaceutical administration forms of the microvesicles of the invention, could be used, administering said product topically is most advantageous in practice; therefore said first or second microvesicles of the invention will be formulated in a pharmaceutical form suitable for its topical administration. Illustrative, non-limiting examples of said pharmaceutical forms include aerosols, solutions, suspensions, emulsions, gels, salves, creams, dressings, patches, ointments, mouthwashes, etc. To that end the first and second pharmaceutical composition of the invention will include the pharmaceutically acceptable vehicles, carriers and/or excipients required for preparing the pharmaceutical administration form of the microvesicles of the invention for topical administration.

Therefore, in a particular embodiment, the pharmaceutical compositions of the invention is a pharmaceutical composition for the topical administration of the microvesicle of the invention comprising said product and a pharmaceutically acceptable vehicle, carrier or excipient suitable for the topical administration of said microvesicle of the invention.

Illustrative, non-limitative, examples of pharmaceutically acceptable vehicles, carriers or excipients suitable for the topical administration of said first or second microvesicles of the invention can be found in galenic pharmacy treatises.

The microvesicles of the invention and combinations thereof and the pharmaceutical compositions of the invention or combinations thereof can be used together with other additional drugs useful in the prevention and/or treatment of a hemorrhagic diathesis (e.g., coagulation factors, human plasma, etc.) to provide a combination therapy. Said additional drugs can be part of the same pharmaceutical composition or, alternatively, they can be provided in the form of a separate composition for their simultaneous or successive (sequential in time) administration with respect to the administration of the pharmaceutical composition of the invention.

The pharmaceutical compositions of the invention can be also placed on a support. Therefore, in another aspect, the invention relates to a product comprising the pharmaceutical composition of the invention or combinations thereof and a support. The term "support", as used herein, refers to a substrate of suitable material allowing depositing the pharmaceutical compositions of the invention thereon, its transport and its release at the desired site, for example, in the site where the pharmaceutical compositions of the invention exercises its therapeutic effect. Said support can be a solid support or a non-solid support, for example, a liquid support or a gaseous support. Illustrative, non-limiting examples of solid supports include dressings, band-aids, compresses, plasters, etc. Illustrative, non-limiting examples of liquid supports include gels, sprays, mouthwashes, etc. Illustrative, non-limiting examples of gaseous supports include air, propellants, etc. This product comprising the microvesicles of the invention or the pharmaceutical compositions of the invention can be obtained by conventional methods, for example, by mixing the microvesicles of the invention and the support. The interaction between the microvesicles of the invention and the support can be a physical or chemical interaction, depending on the nature of the components of the vesicles, the compositions or the pharmaceutical composition of the invention and on the support used.

In other aspect, the invention relates to the microvesicles of the invention or the pharmaceutical compositions of the invention or combinations thereof for the treatment of hemorrhages in a subject, in particular, for the topical treatment of hemorrhages in a healthy subject or in a subject with a hemorrhagic diathesis.

The term "topical treatment", as used herein, refers to the application of the treatment directly at the site where it is required, for example, in discontinuous sections of skin (cuts, etc.) and vascular tissue (ruptured vessels, etc.) in venous and arterial hemorrhage due to open wounds, surgery, etc. and in mucocutaneous and microvascular haemorrhages.

According to this invention and as shown in Example 2, the microvesicles of the invention can act as a pro-coagulant or antihemorrhagic agent, and, consequently, said product can be used to treat or correct hemorrhagic disorders, particularly those hemorrhagic disorders associated with hemorrhagic diathesis.

The term "hemorrhagic diathesis" refers to the process causing a hemostasic disorder and which, as a result, gives rise to the occurrence of a hemorrhagic syndrome which may occasionally occur with extended and excessive bleeding. Hemorrhagic diathesis may be caused by a congenital or acquired coagulopathy and/or by a congenital and acquired platelet disorder.

The term "coagulopathy" refers to a coagulation factor disorder. This disorder may be due to a specific coagulation factor deficiency or deficit, the consequence of which will be the occurrence of a hemorrhagic syndrome, or due to a coagulation factor disorder. The coagulopathy may generally be a congenital coagulopathy or an acquired coagulopathy.

As illustrative, non-limiting examples of congenital coagulopathies, deficiencies of coagulation factors selected from coagulation Factor V (FV), coagulation Factor VII (FVII), coagulation Factor VIII (FVIII), the deficit or deficiency of which causes hemophilia A, coagulation Factor IX (FIX) the deficit or deficiency of which causes hemophilia B, coagulation Factor X (FX), coagulation Factor XI (FXI) the deficit or deficiency of which causes hemophilia C, coagulation Factor XII (FXII), coagulation Factor XIII (FXIII) and their combinations, can be mentioned.

Acquired coagulopathies may have different origins. Illustrative examples include coagulation factor synthesis deficiencies in severe hepatic failure, anticoagulant therapy (such as heparin, low molecular weight heparins, warfarin, coumarin derivatives, dicoumarins, etc.). An alternative mechanism is based on an exaggerated consumption of coagulation factors such that they are not available to form the clot in a bleeding lesion. This mechanism occurs in the disseminated intravascular coagulation syndrome or coagulopathy due to consumption occurring in multiple illnesses such as in severe sepsis damaging the microcirculation endothelium activating platelets and coagulation factors with the formation of multiple microthrombi; in blood invasion by TF such as placental release; in the retention of a dead fetus; in multiple traumas with the crushing of tissues; in poisonous snake bites, etc. In vasculitis, parietal and endothelial damage releases coagulation activators. The consumption of coagulation factors is worsened by lysis of the fibrin of numerous microthrombi due to the action of plasmin with PDF release, which are antiplatelets and anticoagulants.

The term "platelet disorder" refers to a disorder both in the number and in functional ability of platelets, the result of which is the occurrence of a hemorrhagic syndrome. Said platelet disorder may be congenital or acquired.

In a particular embodiment, said platelet disorder is a congenital platelet disorder. Illustrative, non-limiting examples of congenital platelet disorders include Glanzmann's disease, Bernard Soulier disease, Bolin-Jamieson syndrome, Wiskott-Aldrich syndrome, Paris-Trousseau-Jacobsen syndrome, X chromosome thrombocytopenia, Gray platelet syndrome, Sebastian syndrome and Fanconi anemia.

In another particular embodiment, said platelet disorder is an acquired platelet disorder. Illustrative, non-limiting examples of acquired platelet disorders include myeloproliferative disorders, such as thrombocythemia, polycythemia, chronic myelocytic leukemia, etc.; there are functional platelet disorders in myeloid metaplasia with increased bleeding time, glass bead retention defects, platelet aggregation defect, abnormal release, and platelet factor III defect. Functional platelet defects have been found in dysproteinemias in scurvy and in congenital heart disease and cirrhosis.

The terms "acquired coagulopathy" and "acquired platelet disorder" refer to the origin of disorder, which may be iatrogenic or secondary to other disease.

The term "subject" as used herein includes any member of an animal species, including the human species; by way of an illustrative, non-limiting example, said subject can be a mammal, such as a primate, a domestic animal, a rodent, etc., said subject is preferably a man or woman of any age and race. In a particular embodiment, said subject is a human being with no history of hemostasis disorders, such as an individual having no coagulopathies or platelet disorders. In another particular embodiment, said subject is a human being having a history of hemostasis disorders, such as an individual having hemorrhagic diathesis, for example, a coagulopathy, such as a congenital or acquired coagulopathy, or a platelet disorder, such as a congenital or acquired platelet disorder.

Therefore, in a particular embodiment, the invention relates to the microvesicles of the invention or of the pharmaceutical compositions of the invention in the manufacture of a medicament for the topical treatment of hemorrhages in a human being with no history of hemostasis disorders. In another particular embodiment the invention relates to the use the microvesicles of the invention or of the pharmaceutical compositions of the invention in the manufacture of a medicament for the topical treatment of hemorrhaging in a human being having a hemorrhagic diathesis.

Wound Healing-Related Uses

In addition to the role in blood coagulation, TF promotes wound repair and healing (Nakagawa, et al. (1998) Seminars in Thromb. and Hemostasis 24:207-210; Philippart, et al. (2003) The Internatl. J. of Oral and Maxillofacial Implants 3:411-416).

Thus, in another aspect, the invention relates to the use of the microvesicles of the invention or of a pharmaceutical composition of the invention in the manufacture of a medicament for the treatment of wound healing. Alternatively, the invention relates to a microvesicle of the invention or to a pharmaceutical compositions for use in the manufacture of a medicament for the treatment of wound healing. Alternatively, the invention relates to a method for the treatment of wound healing in a patient which comprises the administration to said subject a microvesicles of the invention or a pharmaceutical composition of the invention.

The expression "wound healing" relates to wound healing of any kind and at any site. It can be normal and impaired wound healing. The latter is found in particular in the case of diseases, such as diabetes mellitus, vasculitis, arterial occlusive disease, chronic venous and/or infected ulcer as well as poorly healing gastric ulcer. Impaired wound healing is also found in the case of innervation impairment such as paraplegia, leprosy, neuropathy, etc., and decubital gangrene of persons in need of care. Impaired wound healing will also be given if weak sutures and impaired healing occur after operations, particularly of the intestines and transplantations of skin and other organs, respectively. Impaired wound healing is also found in the case of bone fractures, burns and treatments using steroids.

In the present invention "wound healing" or "wound repair" refers to an intricate process in which the skin (or some other organ) repairs itself after injury As used herein, the term "wound" includes an injury to any tissue, including for example, delayed or difficult to heal wounds, and chronic wounds. Examples of wounds may include both open and closed wounds. The term "wound" may also include for example, injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I wounds limited to the epithelium; ii) Grade II wounds extending into the dermis; iii) Grade III wounds extending into the subcutaneous tissue; and iv) Grade IV (or full-thickness wounds) wounds wherein bones are exposed (e.g., a bony pressure point such as the greater trochanter or the sacrum).

The term "chronic wound" generally refers to a wound that has not healed. Wounds that do not heal within three months, for example, are considered chronic. Chronic wounds include venous ulcers, venous stasis ulcers, arterial ulcers, pressure ulcers, diabetic ulcers, diabetic foot ulcers, vasculitic ulcers, decubitus ulcers, burn ulcers, trauma-induced ulcers, infectious ulcers, mixed ulcers, and pyoderma gangrenosum. The chronic wound may be an arterial ulcer which comprises ulcerations resulting from complete or partial arterial blockage. The chronic wound may be a venous or venous stasis ulcer which comprises ulcerations resulting from a malfunction of the venous valve and the associated vascular disease. In certain embodiments a method of treating a chronic wound is provided where the chronic wound is characterized by one or more of the following AHCPR stages of pressure ulceration: stage 1, stage 2, stage 3, and/or stage.

As used herein, chronic wound may refer to, for example, a wound that is characterized at least in part by one or more of (1) a chronic self-perpetuating state of wound inflammation, (2) a deficient and defective wound extracellular matrix, (3) poorly responding (senescent) wound cells especially fibroblasts, limiting extracellular matrix production, and/or (4) failure of re-epithelialization due in part to lack of the necessary extracellular matrixorchestration and lack of scaffold for migration. Chronic wounds may also be characterized by 1) prolonged inflammation and proteolytic activity leading to ulcerative lesions, including for example, diabetic, pressure (decubitous), venous, and arterial ulcers; 2) progressive deposition of matrix in the affected area, 3) longer repair times, 4) less wound contraction, 5) slower re-epithelialization, and 6) increased thickness of granulation tissue.

Exemplary chronic wounds may include "pressure ulcers." Exemplary pressure ulcers may be classified into 4 stages based on AHCPR (Agency for Health Care Policy and Research, U.S. Department of Health and Human Services) guidelines. A stage I pressure ulcer is an observable pressure related alteration of intact skin whose indicators as compared to the adjacent or opposite area on the body may include changes in one or more of the following: skin temperature (warmth or coolness), tissue consistency (firm or boggy feel) and/or sensation (pain, itching). The ulcer appears as a defined area of persistent redness in lightly pigmented skin, whereas in darker skin tones, the ulcer may appear with persistent red, blue, or purple hues. Stage 1 ulceration may include nonblanchable erythema of intact skin and the heralding lesion of skin ulceration. In individuals with darker skin, discoloration of the skin, warmth, edema, induration, or hardness may also be indicators of stage 1 ulceration. Stage 2 ulceration may be characterized by partial thickness skin loss involving epidermis, dermis, or both. The ulcer is superficial and presents clinically as an abrasion, blister, or shallow crater. Stage 3 ulceration may be characterized by full thickness skin loss involving damage to or necrosis of subcutaneous tissue that may extend down to, but not through, underlying fascia. The ulcer presents clinically as a deep crater with or without undermining of adjacent tissue. Stage 4 ulceration may be characterized by full thickness skin loss with extensive destruction, tissue necrosis, or damage to muscle, bone, or supporting structures (e.g., tendon, joint capsule). In certain embodiments a method of treating a chronic wound is provided where the chronic wound is characterized by one or more of the following AHCPR stages of pressure ulceration: stage 1, stage 2, stage 3, and/or stage 4.

Exemplary chronic wounds may also include "decubitus ulcers." Exemplary decubitus ulcers may arise as a result of prolonged and unrelieved pressure over a bony prominence that leads to ischemia. The wound tends to occur in patients who are unable to reposition themselves to off-load weight, such as paralyzed, unconscious, or severely debilitated persons. As defined by the U.S. Department of Health and Human Services, the major preventive measures include identification of high-risk patients; frequent assessment; and prophylactic measures such as scheduled repositioning, appropriate pressure-relief bedding, moisture barriers, and adequate nutritional status. Treatment options may include for example, pressure relief, surgical and enzymatic debridement, moist wound care, and control of the bacterial load. In certain embodiments a method of treating a chronic wound is provided wherein the chronic wound is characterized by decubitus ulcer or ulceration, which results from prolonged, unrelieved pressure over a bony prominence that leads to ischemia.

Chronic wounds may also include "arterial ulcers." Chronic arterial ulcers are generally understood to be ulcerations that accompany arteriosclerotic and hypertensive cardiovascular disease. They are painful, sharply marginated, and often found on the lateral lower extremities and toes. Arterial ulcers may be characterized by complete or partial arterial blockage, which may lead to tissue necrosis and/or ulceration. Signs of arterial ulcer may include, for example, pulselessness of the extremity; painful ulceration; small, punctate ulcers that are usually well circumscribed; cool or cold skin; delayed capillary return time (briefly push on the end of the toe and release, normal color should return to the toe in about 3 seconds or less); atrophic appearing skin (for example, shiny, thin, dry); and loss of digital and pedal hair. In certain embodiments a method of treating a chronic wound is provided wherein the chronic wound is characterized by arterial ulcers or ulcerations due to complete or partial arterial blockage.

Exemplary chronic wounds may include "venous ulcers." Exemplary venous ulcers are the most common type of ulcer affecting the lower extremities and may be characterized by malfunction of the venous valve. The normal vein has valves that prevent the backflow of blood. When these valves become incompetent, the backflow of venous blood causes venous congestion. Hemoglobin from the red blood cells escapes and leaks into the extravascular space, causing the brownish discoloration commonly noted. It has been shown that the transcutaneous oxygen pressure of the skin surrounding a venous ulcer is decreased, suggesting that there are forces obstructing the normal vascularity of the area. Lymphatic drainage and flow also plays a role in these ulcers. The venous ulcer may appear near the medial malleolus and usually occurs in combination with an edematous and indurated lower extremity; it may be shallow, not too painful and may present with a weeping discharge from the affected site. In certain embodiments a method of treating a chronic wound is provided wherein the chronic wound is characterized by venous ulcers or ulcerations due to malfunction of the venous valve and the associated vascular disease. In certain embodiments a method of treating a chronic wound is provided wherein the chronic wound is characterized by arterial ulcers or ulcerations due to complete or partial arterial blockage.

Exemplary chronic wounds may include "venous stasis ulcers." Stasis ulcers are lesions associated with venous insufficiency are more commonly present over the medial malleolus, usually with pitting edema, varicosities, mottled pigmentation, erythema, and nonpalpable petechiae and purpura. The stasis dermatitis and ulcers are generally pruritic rather than painful. Exemplary venous stasis ulcers may be characterized by chronic passive venous congestion of the lower extremities results in local hypoxia. One possible mechanism of pathogenesis of these wounds includes the impediment of oxygen diffusion into the tissue across thick perivascular fibrin cuffs. Another mechanism is that macromolecules leaking into the perivascular tissue trap growth factors needed for the maintenance of skin integrity. Additionally, the flow of large white blood cells slows due to venous congestion, occluding capillaries, becoming activated, and damaging the vascular endothelium to predispose to ulcer formation. In certain embodiments a method of treating a chronic wound is provided wherein the chronic wound is characterized by venous ulcers or ulcerations due to malfunction of the venous valve and the associated vascular disease. In certain embodiments a method of treating a chronic wound is provided wherein the chronic wound is characterized by venous stasis ulcers or ulcerations due to chronic passive venous congestion of the lower extremities and/or the resulting local hypoxia.

Exemplary chronic wounds may include "diabetic ulcers." Diabetic patients are prone to ulcerations, including foot ulcerations, due to both neurologic and vascular complications. Peripheral neuropathy can cause altered or complete loss of sensation in the foot and/or leg. Diabetic patients with advanced neuropathy loose all ability for sharp-dull discrimination. Any cuts or trauma to the foot may go completely unnoticed for days or weeks in a patient with neuropathy. It is not uncommon to have a patient with neuropathy notice that the ulcer "just appeared" when, in fact, the ulcer has been present for quite some time. For patients of neuropathy, strict glucose control has been shown to slow the progression of the disease. Charcot foot deformity may also occur as a result of decreased sensation. People with "normal" feeling in their feet have the ability to sense automatically when too much pressure is being placed on an area of the foot. Once identified, our bodies instinctively shift position to relieve this stress. A patient with advanced neuropathy looses this ability to sense the sustained pressure insult, as a result, tissue ischemia and necrosis may occur leading to for example, plantar ulcerations. Additionally, microfractures in the bones of the foot, if unnoticed and untreated, may result in disfigurement, chronic swelling and additional bony prominences. Microvascular disease is one of the significant complications for diabetics, which may also lead to ulcerations. In certain embodiments a method of treating a chronic wound is provided wherein the chronic wound is characterized by diabetic foot ulcers and/or ulcerations due to both neurologic and vascular complications of diabetes.

Exemplary chronic wounds can include "traumatic ulcers." Formation of traumatic ulcers may occur as a result of traumatic injuries to the body. These injuries include, for example, compromises to the arterial, venous or lymphatic systems; changes to the bony architecture of the skeleton; loss of tissue layers-epidermis, dermis, subcutaneous soft tissue, muscle or bone; damage to body parts or organs and loss of body parts or organs. In certain embodiments, a method of treating a chronic wound is provided wherein the chronic wound is characterized by ulcerations associated with traumatic injuries to the body.

Exemplary chronic wounds can include "burn ulcers", including 1st degree burn (i.e. superficial, reddened area of skin); 2nd degree burn (a blistered injury site which may heal spontaneously after the blister fluid has been removed); 3rd degree burn (burn through the entire skin and usually require surgical intervention for wound healing); scalding (may occur from scalding hot water, grease or radiator fluid); thermal (may occur from flames, usually deep burns); chemical (may come from acid and alkali, usually deep burns); electrical (either low voltage around a house or high voltage at work); explosion flash (usually superficial injuries); and contact burns (usually deep and may occur from muffler tail pipes, hot irons and stoves). In certain embodiments, a method of treating a chronic wound is provided wherein the chronic wound is characterized by ulcerations associated with burn injuries to the body. Exemplary chronic wounds can include "vasculitic ulcers." Vasculitic ulcers also occur on the lower extremities and are painful, sharply marginated lesions, which may have associated palpable purpuras and hemorrhagic bullae. The collagen diseases, septicemias, and a variety of hematological disorders (e.g., thrombocytopenia, dysproteinemia) may be the cause of this severe, acute condition. Exemplary chronic wounds can include pyoderma gangrenosum. Pyoderma gangrenosum occurs as single or multiple, very tender ulcers of the lower legs. A deep red to purple, undermined border surrounds the purulent central defect. Biopsy typically fails to reveal a vasculitis. In half the patients it is associated with a systemic disease such as ulcerative colitis, regional ileitis, or leukemia. In certain embodiments, a method of treating a chronic wound is provided wherein the chronic wound is characterized by ulcerations associated with pyoderma gangrenosum. Exemplary chronic wounds can include infectious ulcers. Infectious ulcers follow direct inoculation with a variety of organisms and may be associated with significant regional adenopathy. *Mycobacteria* infection, anthrax, diphtheria, blastomyosis, sporotrichosis, tularemia, and cat-scratch fever are examples. The genital ulcers of primary syphilis are typically nontender with a clean, firm base. Those of chancroid and granuloma inguinale tend to be ragged, dirty, and more extravagant lesions. In certain embodiments, a method of treating a chronic wound is provided wherein the chronic wound is characterized by ulcerations associated with infection. As used herein, the term "dehiscent wound" refers to a wound, usually a surgical wound, which has ruptured or split open. In certain embodiments, a method of treating a wound that does not heal at the expected rate is provided wherein the wound is characterized by dehiscence.

The suitable carriers that can be used have been described previously. The medicament that comprises the first or a second micorvesicle or the invention and a combination thereof, can also comprise other compounds used for wound healing.

Angiogenesis-Related Uses

In addition to its role in blood coagulation, TF plays a role in angiogenesis. This was discovered when it was found that mice in which TF had been genetically knocked out were unable to develop beyond embryonic day 9-10 due to the failure to develop blood vessels (Carmeliet, et al., 1996, Nature 383:73-75; Bugge et al., 1996, Proc. Natl. Acad. Sci. USA, 93: 6258-6263; Toomey, et al., 1996, Blood 88: 1583-1587). Further studies have demonstrated that activation of coagulation proteases can lead to activation of the protease activated receptors leading to increased production of vascular endothelial growth factors which stimulate angiogenesis (Richard, et al., 2002, Oncogene 20: 1556-1562; Milia, et al., 2002, Circ. Res. 91:346-352). In addition, the over-expression of TF on tumor cells promotes tumor growth, vascularization and metastasis (Mueller, et al., 1992, Proc. Natl. Acad. Sci. USA, 89: 11832-11836).

Thus, in another aspect, the invention relates to the use of a first or a second microvesicles of the invention or combinations thereof, a first or a second compositions or the invention or combinations thereof, or a first or a second pharmaceutical compositions of the invention or combinations thereof in the manufacture of a medicament for the treatment of an disease associated to deficient angiogenesis.

Angiogenesis is the process by which new blood vessels or lymphatic vessels form by developing from pre-existing vessels. The term "disease associated to deficient angiogenesis", as used herein, relates to diseases wherein which can be cured by activating vessel formation. The expression "vessel formation" relates to a vessel formation of any kind and at any site. The promotion of vessel formation may be useful in a number of clinical conditions. For example, the pro-angiogenic TF-bearing microvesicles of the invention may be used to promote angiogenesis of collateral vasculature in myocardial tissue during or following ischaemic disease, myocardial infarction or following coronary bypass surgery. Other diseases or conditions which may be treated by the provision of the TF-bearing microvesicles of the invention include vascular disease and/or ischaemic disease causing pathology of the peripheral or central nervous system. Such conditions/diseases may include cerebrovascular accidents, e.g. caused by clot occlusions or by rupture of aneurysms, or general/localised ischemia causing neuronal death or peripheral functional impairment such as in motor or sensory functions or speech impairment, ischemic cardiomyopathy, or peripheral arterial disease, such as chronic limb ischemia claudication (skeletal muscle), rest pain/ischemic ulceration/gangrene. Moreover, the promotion of vessel formation is adequate for replacing impaired, e.g., old, blood vessels. They can be present, e.g., in the brain or heart, so that an apoplexy or infarction can be prevented or treated. Precautions can also be taken against presbyphrenia. In addition, it relates to a vessel formation for treating arteriosclerosis, Crohn's disease and ulcerative colitis, diabetic retinopathy and deep venous thrombosis of the legs/ulcus cruris as well as the prevention of relapses.

A patient suffering from a disease associated to deficient angiogenesis can be treated with a microvesicle of the invention or with a pharmaceutical composition of the invention or combinations thereof in combination with an anti-angiogenesis therapy, an anti-cancer therapy, or other therapy known to treat the disease or condition.

As used herein, "therapy" includes but is not limited to a known drug. Cancers treatable by the methods of the present invention include all solid tumor and metastatic cancers, including but not limited to those selected from the group consisting of bladder, breast, liver, bone, kidney, colon, ovarian, prostate, pancreatic, lung, brain and skin cancers. The invention includes but is not limited to treatment of cancer with a first or a second microvesicle of the invention or combination thereof, alone, in combination with chemotherapy, or in combination with radiation therapy by methods known in the art (see U.S. Pat. No. 6,596,712).

Kits of the Invention

In another aspect the invention relates to a kit comprising the microvesicle of the invention as well as to the use of said microvesicle for determining an anticoagulant therapy factor in a sample.

As used herein, the term "kit" is used in reference to a combination of articles that facilitate a process, method, assay, analysis or manipulation of a sample. These kits provide the materials necessary for carrying out the methods described in the present invention.

The term "anticoagulant therapy factor", as used herein, refers to a parameter which is useful in deciding whether a patient requires an anticoagulant therapy. Anticoagulant therapy factors include, without limitation, prothrombin time (PT), International Normalized Ratios (INR), modified ATF (MATF), corrected ATF (CATF), prothrombin ratio (PR) and a fibrinogen transformation rate (FTR).

The term "prothrombin time", "PT" or grammatical equivalents thereof as used herein means tests for blood coagulation time that are usable to monitor treatment of individuals who are at risk of excessive blood clotting (thrombosis). The prothrombin time refers to the period of time calculated from the addition of tissue factor—calcium to a sample to the point where the conversion of fibrinogen to fibrin begins. Prothrombin time is typically determined by contacting different dilutions of normal human plasma (preferably 1:2, 1:4, 1:10, 1:20 and 1:40 dilutions in 0.15M NaCl) to yield samples having reduced factor activity (50, 25, 10, 5 and 2.5%, respectively. The first or second vesicles of the invention are added to the samples and the time the sample takes to clot is measured optically.

The prothrombin ratio (PR), a used herein, refers to another measurement of blood coagulation which is calculated by dividing the PT of a patient plasma by the PT of a pool of plasmas from normal individuals.

The kits and uses of the invention can be used in the coagulation laboratory. Variants of this test have a number of uses (White, et al., Hemostasis and Thrombosis, Basic Principles and Clinical Practice, Coleman, et al., eds., J. B. Lippencott Co., Philadelphia, pp. 1048-1060, 1987). One use is to assess deficiencies in the extrinsic pathway of coagulation (factors VII, X, V, and prothrombin). A second use is to monitor patients undergoing long term oral anticoagulant therapy for disorders such as recurrent venous thrombosis and cancer (Hirsh, J., Seminars in Thrombosis and Hemostasis, 12:1-11, 1986). A third use is to evaluate liver dysfunction.

The therapeutic range of anticoagulant therapy is based on the avoidance of bleeding and thrombolic complications. When monitoring oral anticoagulant therapy, as well as for a variety of other conditions by the PT test, an elongation of prothrombin time by a factor of 2 is most desirable for long term therapy (O'Reilly, Hemostasis and Thrombosis, Basic Principles and Clinical Practice, Coleman, et al., eds., J. B. Lippencott Co., Philadelphia, pp. 1367-1372, 1987). This elongation factor is defined as the prothrombin ratio (PR) and is calculated by dividing the PT of a patient plasma by the PT of a pool of plasmas from normal individuals. A higher PR indicates a more sensitive PT reagent. The benefits of a more sensitive reagent for monitoring anticoagulation therapy is the use of lower doses of anticoagulant drug. These lower doses still provide adequate protection against thromboembolic disease while minimizing bleeding complications.

The kit may comprise, in addition, a packaging which allows maintaining the reagents within determined limits. Suitable materials for preparing such packings include glass, plastic (polyethylene, polypropylene, polycarbonate and the like), bottles, vials, paper, sachets and the like. The kit of the invention can additionally contain instructions for using the reagent or reagents in the method of the invention. Said instructions can be found in the form of printed material or in the form of an electronic support which can store instructions such that they can be read by a subject, such as electronic storage media (magnetic disks, tapes and the like), optical media (CD-ROM, DVD) and the like. The media can additionally or alternatively contain Internet websites providing said instructions.

The invention is described in detail by way of the following examples which are to be considered as merely illustrative and not limitative of the scope of the invention.

EXAMPLES

Methods

Coagulation Assays in Plasma

Spontaneous procoagulant activity (unstimulated) in plasma was measured by means of a two-step coagulation assay in a 4-channel coagulometer (Start 4, Diagnostica Stago). Briefly, 50 µl of platelet-poor plasma were added to the already tempered cuvettes and 50 µl of the sample (TF, or distilled water as control) were added. This mixture was left to incubate for 60 seconds at 37° C. and 50 µl of 25 mM calcium chloride were immediately added and the coagulation time was determined in seconds in the coagulometer, verified by formation of the clot. Platelet-poor plasmas were obtained by centrifugation and number of platelets was determined by Coulter.

The procoagulant effect of TF on coagulation factors deficient plasmas (FVIII, FIX or FXI) corresponding to Haemophilia A, B or C, respectively, was investigated by using commercial plasmas (Dade Behring Marburg GmbH) depleted by means of immunoaffinity techniques. In each case, the final content of said coagulation factors was less than 1%.

The procoagulant effect in a thrombocytopenic like condition was investigated in plasma depleted from platelet with a sequential centrifugation process.

Coagulation Assays in Whole Blood

Procoagulant activity in non-anticoagulated whole blood was determined by means of a coagulation method. The different agents (mTF) to be studied were added in 0.2 ml final volume to 0.8 ml of non-anticoagulated whole blood and coagulation time was measured with a chronometer from the beginning of the extraction until a stable and consolidated blood clot appeared. The effect of the different agents was evaluated by means of their shortening or lengthening of blood coagulation times.

Whole blood samples were obtained from patients or healthy volunteers.

Example 1

Production of a Pro-Coagulant Product Based on the Expression of the Full-Length TF His-Tag Modified Protein in Yeast (TT-173).

The yeast episomal vector described in WO2008080989 and comprising the URA3 gene, the ampicillin resistance gene, the yeast 2µ origin of replication, the glyceraldehyde-3-phosphate dehydrogenase (GPD) promoter and the yeast transcription termination signal of the phosphoglycerate kinase was used to clone under the control of the GPD promoter a cDNA coding for the mature hTF protein (aa 33-295 of SEQ ID NO:1) with 18 extra nucleotides (coding for six histidines) at the 3' end and an Asn124Ala mutation which inactivates one of the potential N-glycosylation sites in the native hTF sequence (SEQ ID NO:6).

After transformation of the yeast strain T73 ura3-, strains capable of growing in uracil-free media were collected and tested for their ability to express hTF by Western-blot analysis of the yeast extracts essentially as described in WO2008080989.

In order to evaluate the possibility of scaling at pre-industrial level the production of yeast extracts, fermentations in a 2 liter bioreactor (Biostat B-2L. BRAUN) were carried out by growing the cells at 30° C. at a stirring speed of 250-300 rpm, a pH of 4.5 and an air flow of 6 L/m. The culture medium was CSM-URA:0.78 g/L; YNB: 6.7 g/L; Sucrose: 20 g/L. Fermentation was stopped when culture reached an OD of 8.0.

The product resulting from the fermentation was collected by centrifugation at 3,000 rpm (1,200×g) for 10 min and resuspended in 200 ml of lysis buffer (20 mM Phosphate buffer (pH 7.4), 50 mM NaCl). Yeasts were homogenized by high pressure (1,000 bar ($10^8$ Pa)) (homogenizer NIRO SOAVIS. Panda 2K), and the homogenate centrifuged at 13,000 rpm (13,000×g) for 30 min at 4° C. The pellet was discarded, and the supernatant named as clarified yeast extract (CYE) was collected.

This CYE containing rTF was fractionated by successive steps of tangential flow filtration in a Crossflow Filtration System (Sartorius sartoflow Slice 200 Benchtop) using filters with a gradual reduction on the pore size (0.45 μm, 0.2 μm and 0.1 μm membranes (Sartorius, polysulfone).

The pro-coagulant activity of the different retentates and permeates obtained from four independent CYE after the successive steps of filtration is represented on Table 1. The presence of TF in each of the four MFR 0.1 fractions is shown in FIG. 1.

TABLE 1

Procoagulant activity average of microfiltrate retentates (MFR), and microfiltrate permeates (MFP) from four independent CYE after tangential flow filtration. The coagulation assay procedure is defined in Methods.

|  | Activity sec |
|---|---|
| CYE | 23.5 |
| MFR 0.45 | 23.6 |
| MFP 0.45 | 24.0 |
| MFR 0.2 | 24.3 |
| MFP 0.2 | 24.9 |
| MFR 0.1 | 18.1 |
| MFP 0.1 | >300 |

In this way, a purified yeast vesicle preparation was obtained (hereinafter referred to as TT-173) having procoagulant properties as determined using different in vitro and in vivo assays essentially as described in WO2008080989. This result indicates that the use of tangential flow filtration procedures used to purify the TT-173 product allows the recovery of biologically active hTF which is associated to yeast-derived membrane microvesicles.

Example 2

Enhancement of TT-173 Bioactivity by the Addition of PS 2.1 Effect of Phosphatydilserine (PS) on TT-173 Bioactivity PS (0.1 mM) was added to TT-173 and the mixture incubated for up to 4 h. At different time points, starting from the time in which PS was added (time 0), an aliquot of the TT-173/PS mixture was checked for clotting activity in a standard coagulometric assay.

Figure 2:
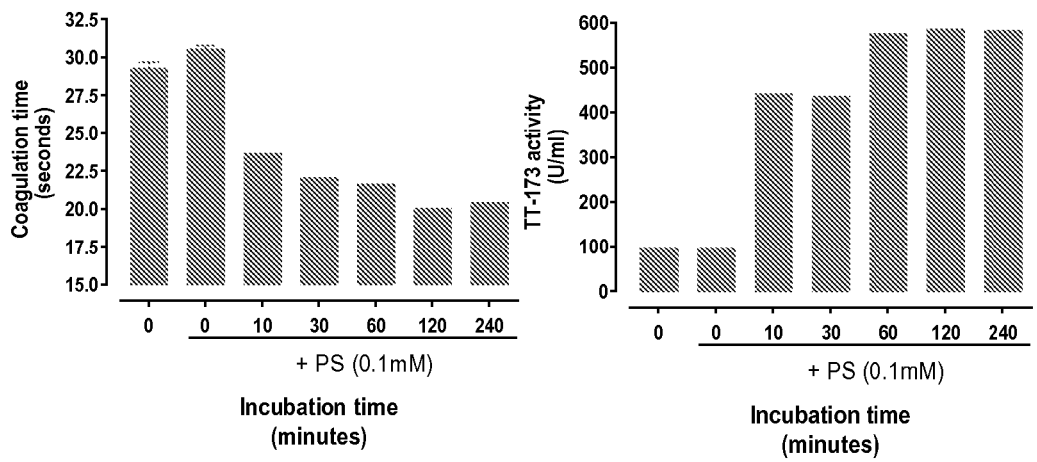
FIG. 2. Pro-coagulant activity of TT-173 after incubation with PS. A.—In order to test the effect of PS on TT-173 bioactivity, PS (0.1 mM) was added to TT-173 (1 mL) and the mixed solution was maintained at R/T during the experiment. At the different time points represented in the figure, one aliquot of the mixture (10 μL) was added to warmed cuvettes containing 130 μl of normal platelet-poor plasma. 20 μl of calcium chloride (100 mM) were immediately added, and the coagulation time (in seconds) was determined with the aid of a coagulometer (Stago). The experiment was stopped after 300 seconds (pooled plasma from 5 donors). B.—Results obtained as described in A were also represented as Units/mL. 1 Unit is defined as the amount of TT-173 required to coagulate normal pooled plasma in 30 seconds in a standard coagulometric assay (130 μl of plasma, 20 μl of Calcium Chloride (100 mM) and 10 μl of product).

The results, presented in FIG. 2, clearly show that addition of PS reduces coagulation time in approximately 10 s (Panel A), which corresponds to an increment in specific activity of six fold (panel B), and that this amplification is time-dependent, reaching a maximum 1 to 2 h after PS addition.

The negligible effect of PS by itself on coagulation time (not shown), and the increase in the observed boosting effect during the first hour after its addition to TT-173, suggested that some interaction between TT-173 and PS occurred, and that this interaction was important to accelerate the clotting time.

This effect was specific for negatively charged phospholipids since the addition of non-charged or positively-charged phospholipids at similar concentrations (0.1 mM) does not induce a detectable increment in clotting activity of TT-173. In particular, neither of Phosphatidyl serine (PS), Phosphatidylethanolamine (PE), Sphingomyelin (SM), or Phosphatidylcholine (PC) induced a detectable increment in clotting activity.

Figure 3:
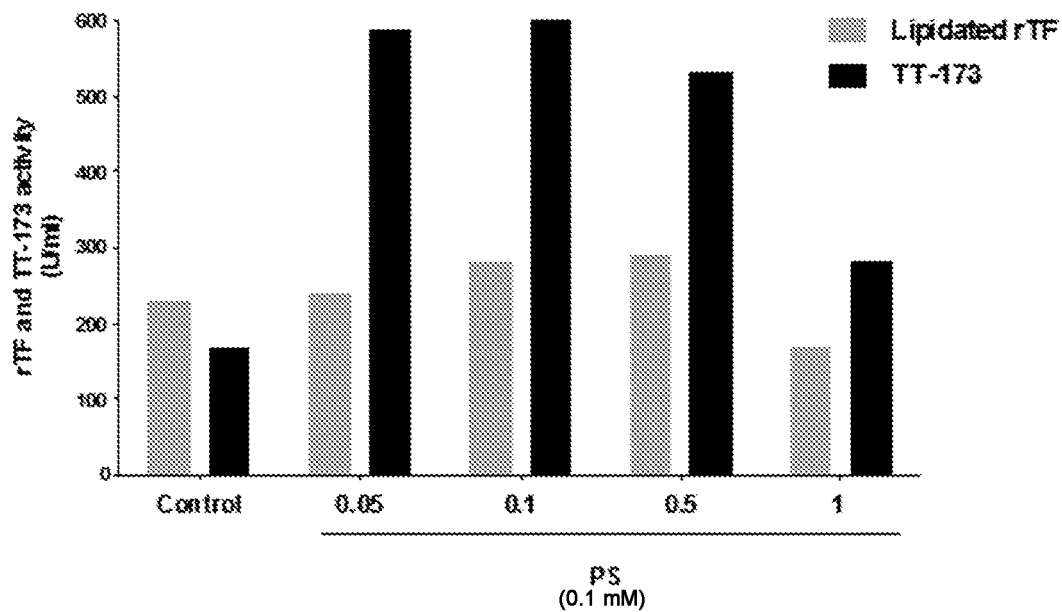
FIG. 3. Pro-coagulant activity of TT-173 or lipidated rTF after incubation with different concentrations of PS. To test the effect of PS on either TT-173 or relipidated rTF bioactivity, PS (at the concentrations denoted in the figure) were added to either TT-173 (1 mL) or relipidated rTF. Both mixed solutions were maintained at R/T for 2 h. After this time, one aliquot of each mixture (10 μL) was added to warmed cuvettes containing 130 μl of normal platelet-poor plasma. Immediately after, 20 μl of calcium chloride (100 mM) were added, and the coagulation time (in seconds) was determined with the aid of a coagulometer (Stago). The experiment was stopped after 300 seconds (pooled plasma from 5 donors). The results obtained are represented as Units/mL.

It was then tested whether the PS/TT-173 interaction was restricted to yeast-derived structures or whether it could be recreated in artificially-made vesicles. To test this, PS was added at different concentrations (ranging from 0.05 to 1 mM) to aliquots with equivalent clotting activity of either TT-173 or in vitro relipidated rTF. After incubation of the mixture for 2 h at R/T, samples from both rTF-containing products were tested for their clotting activity. The results are shown in FIG. 3. As observed before, addition of PS to TT-173 clearly increases the activity approximately six fold. This effect was observed in the concentration range from 0.05 to 0.5 mM of PS. At higher concentrations (1 mM) PS produced a clear inhibitory clotting effect. Surprisingly, addition of PS to relipidated rTF did not result in an appreciable increase in procoagulant activity, at any of the PS concentrations used. Again, the higher concentration of PS tested (1 mM) produced a clear inhibitory effect. This inhibitory effect by the higher concentration of PS on either TT-173 or relipidated rTF samples, could be explained if PS vesicles at high concentrations interacts efficiently with soluble coagulation factors, sequestering them, and thus limiting their interaction with rTF-containing vesicles.

Figure 4:
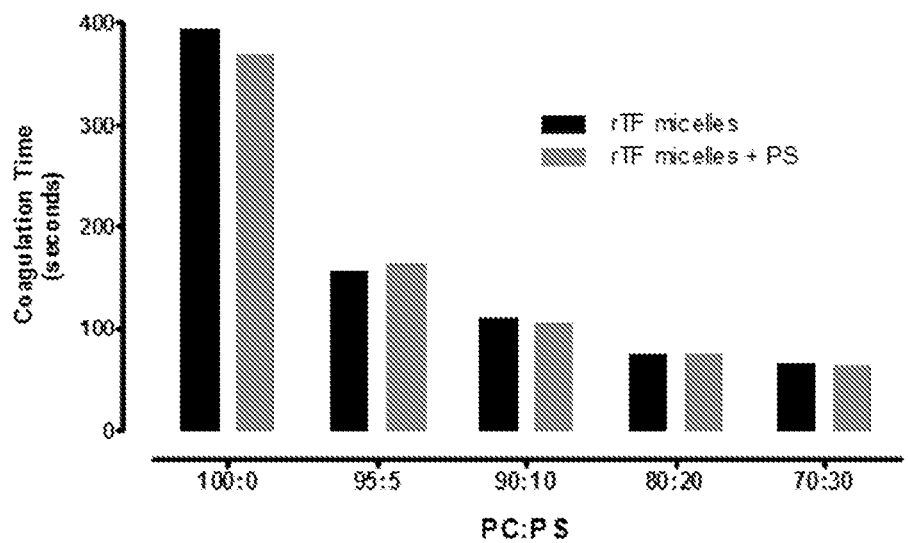
FIG. 4. Procoagulant activity of rTF when embedded into suitable phospholipid vesicles. Commercial purified rTF was relipidated into vesicles containing phosphatidyl choline/phosphatidyl serine (PC/PS) following the standardized method described by Mimms et al. (Biochemistry 20, 833. 1981). Briefly, 100 ng of rTF (American Diagnostica Inc. Stanford, Conn., USA) were incubated with: PC/PS (Sigma Aldrich Inc, Saint Louis, Mo., USA) at the indicated PC:PS proportions (100:0, 95:5, 90:10, 80:20, 70:30) (2.6 mM final concentration), and detergent (N-Octyl-β-D-galactopiranoside, 40 mM final concentration). The mixture was homogenized, and extensively dialyzed (during 48 h with several changes of buffer). By this procedure, detergent is slowly removed and lipid micelles containing rTF are spontaneously produced. After this relipidation procedure, the rTF-containing micelles were tested for their procoagulant activity (Blue bars). In parallel, the different rTF-containing micelles were incubated for 2 h with PS at a final concentration of 0.1 mM. After this time, micelles containing extra PS were also tested for procoagulant activity. Coagulometric analyses were carried out as follows: Aliquots (10 μl) of the relipidated rTF with amount of PC/PS vesicles, were added to warmed cuvettes containing 130 μl of normal platelet-poor plasma. Immediately after, 20 μl of calcium chloride (100 mM) were added, and the coagulation time (in seconds) was determined with the aid of a coagulometer (Diagnostica Stago, Inc. NJ, USA).

This was further confirmed by testing the effect on the clotting activity as a result of adding increasing PS concentrations to already pre-existing rTF-containing micelles having different PC to PS ratios. The optimal concentration of phospholipids to restore full rTF activity is well established, and it corresponds to phosphatidylcholine (PC) to phosphatidylserine (PS) ratios from 80:20 to 70:30. FIG. 4 (black bars), shows a typical clotting experiment in which rTF was relipidated with PC alone (concentration PC:PS of 100:0), or with increasing concentration ratios of PS related to PC (concentrations PC:PS of 95:5, 90:10 and 80:20 respectively). The result clearly shows that the addition of increasing amounts of PS results in decreased coagulation times. However, when extra PS was added to pre-existing micelles, at any of the PC:PS ratios tested, did not exert any increment in clotting activity (FIG. 4, grey bars).

Figure 5:
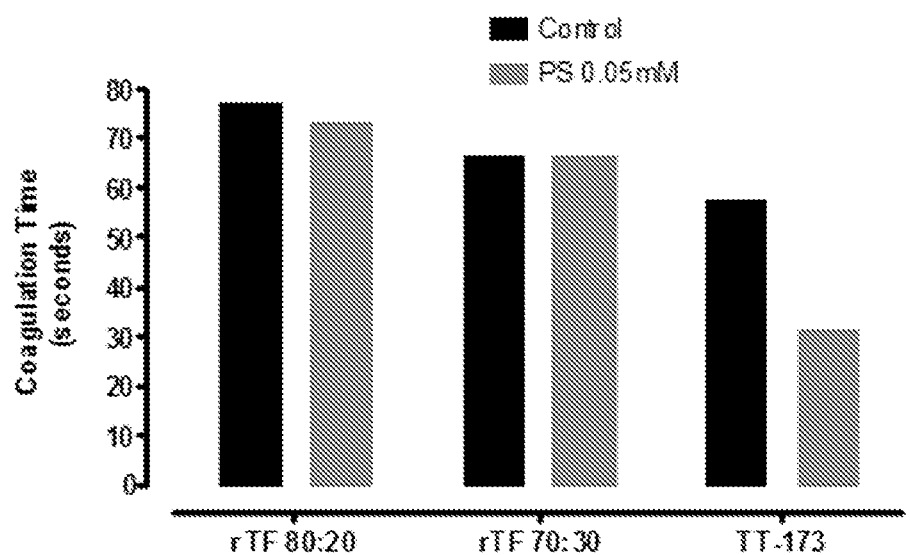
FIG. 5. Effect of addition of PS over different rTF-containing vesicles. Two aliquots (2 mL each) from either: i) relipidated rTF at a PC:PS concentration ratio of 80:20, ii) relipidated rTF at a PC:PS concentration ratio of 70:30 or iii) TT-173 vesicles isolated from recombinant yeast expressing TF were prepared at 4° C. PS at a concentration of 0.1 mM was added to one of the aliquots of each of the rTF-containing vesicles, and incubated at R/T for 2 h. During this time, the other aliquot was kept at 4° C. After that, both aliquots from each rTF-containing vesicles were tested for procoagulant activity as described in figure legend 1.

To provide further evidence that the effect observed is restricted to eukaryotic-derived structures, and could not be recreated in artificially-made vesicles by relipidation, PS was added at concentration 0.1 mM to aliquots with equivalent clotting activity of either TT-173 vesicles produced in yeast cells or in vitro relipidated rTF at PC:PS ratios of 80:20 and 70:30. After incubation of the different vesicles with PS for 2 h at R/T, samples from the different rTF-containing products were tested for their clotting activity. The results are shown in FIG. 5. As observed, addition of PS to TT-173 from yeast origin, clearly reduced the clotting time, whereas as expected, addition of PS to relipidated rTF did not result in an appreciable increase in procoagulant activity, at any of the PC:PS proportions used for relipidation.

Figure 6:
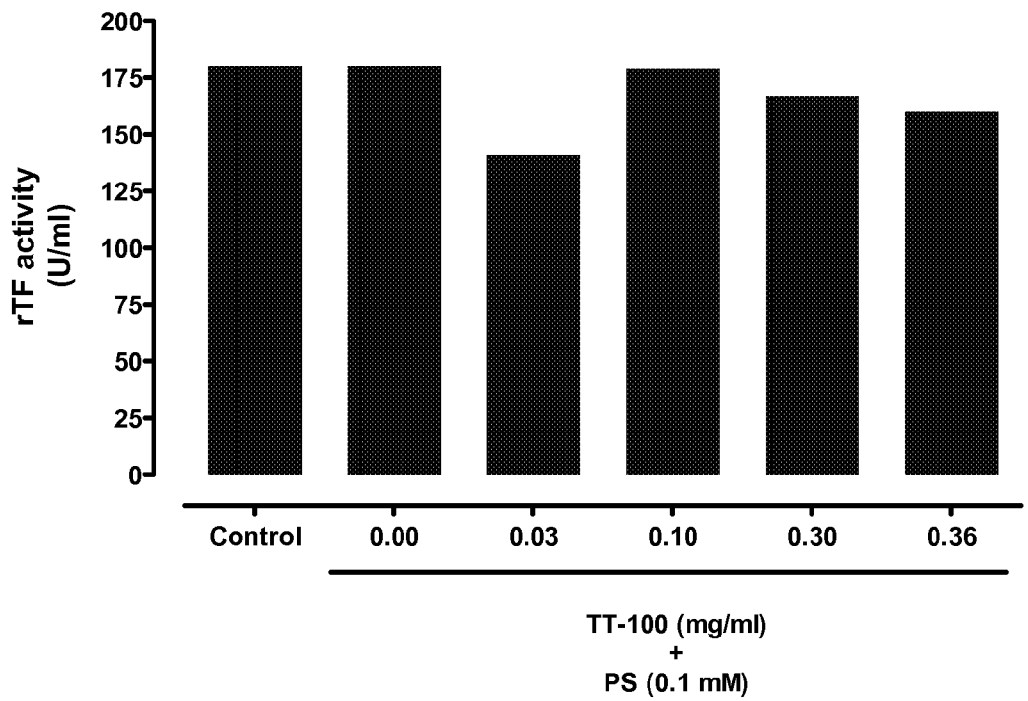
FIG. 6. Pro-coagulant activity of relipidated rTF after incubation with PS and different concentrations of TT-100. Aliquots (10 μl) of relipidated rTF (0.3 μg/ml) incubated for 2 h with PS (0.1 mM) and different concentrations of TT-100 (0, 0.03, 0.1, 0.3, and 0.36 mg/ml) were added to warmed cuvettes containing 130 μl of normal platelet-poor plasma. Immediately after, 20 μl of calcium chloride (100 mM) were added, and the time of coagulation (in seconds) was determined with the aid of a coagulometer.

To test whether addition of PS was effective only when associated to yeast derived vesicles, an experiment was done using relipidated rTF and TT-100 vesicles (microvesicles obtained from recombinant yeast transformated with the plasmid without the TF protein sequence), obtained from non-recombinant yeast following the same production procedure as TT-173. Aliquots of relipidated rTF were mixed with different concentrations of TT-100 vesicles that were previous incubated with PS (0.1 mM) for 2 h. After 30 m the clotting activity of each aliquot was determined. The results (FIG. 6) clearly show that independently of the amount of TT-100 used, the mixture TT-100/PS does not have a detectable effect on relipidated rTF.

This result demonstrates that the effect of PS on clotting activity is dependent on its association with yeast-derived vesicles, and that these vesicles must contain rTF.

In view of the above results, the boosting clotting effect induced by PS in TT-173 (see FIGS. 2, 3 and 5) could be explained if: i) PS facilitates the interaction between rTF and FVII, inducing a more suitable scaffolding for the interaction; ii) added PS induces structural effects in the vesicles generating areas enriched in PS, as in activated platelets, more suitable for prothrombinase complex formation; or iii) a combination of both effects.

Figure 7:
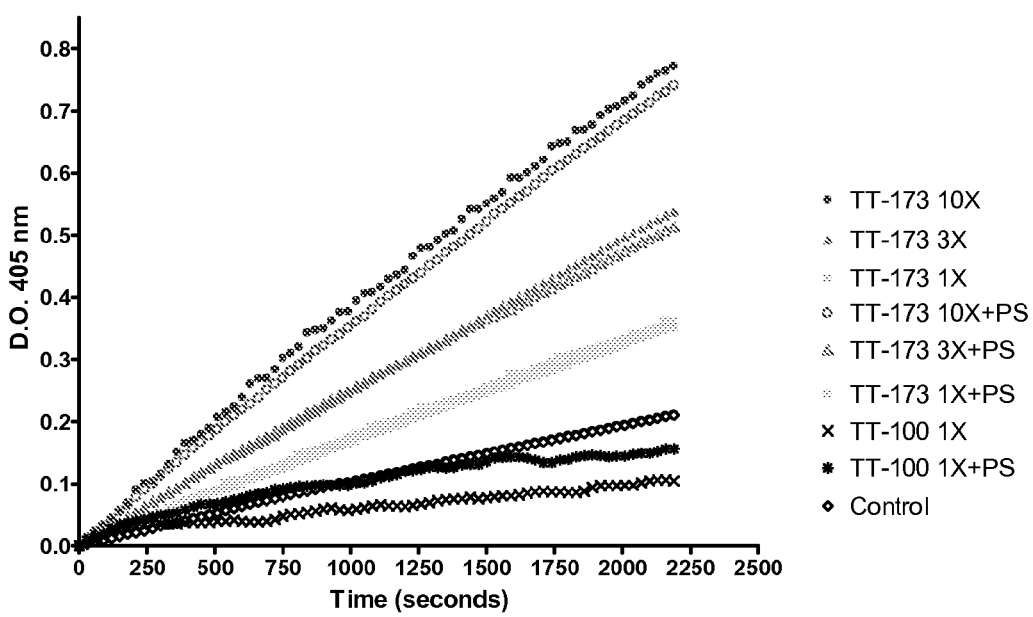
FIG. 7. Amidolytic activity of FVIIa. To quantify the enzymatic activity of the TF:FVIIa catalytic complex, a standard chromogenic assay was carried out using the substrate S-2238. The TF:FVIIa activity is measured by the difference in absorbance (optical density) between the substrate S-2238 and the resulting product of processing p-nitroanilina (pNA). The rate of pNA formation is proportional to the enzymatic activity and it is conveniently determined with a photometer. In this experiment, different concentrations of TT-173, containing or not PS, were tested by its ability to interact with FVIIa and in the presence of S-2238 to produce detectable pNA.

To test the possible effect of PS on rTF:FVII interaction, a standard amidolytic assay defined to quantify the enzymatic activity of the TF:FVII complex was used. For this experiment, three concentrations of TT-173 with or without added PS were incubated with two different concentrations of purified commercial FVIIa. After addition of FVIIa to TT-173, the TF/FVIIa activity was detected by the capability of the complex to enzymatically transform the specific chromogenic substrate S-2288. As shown in FIG. 5, there was no appreciable differences in the amidolytic activity between TT-173 with or without PS at the three concentrations of TT-173 tested, and at both concentrations of FVIIa used, 50 nM (not shown) or 500 nM (FIG. 7). These results clearly demonstrate that addition of PS to TT-173 do not exert a significant effect on the initial rTF-FVII interaction.

Figure 8:
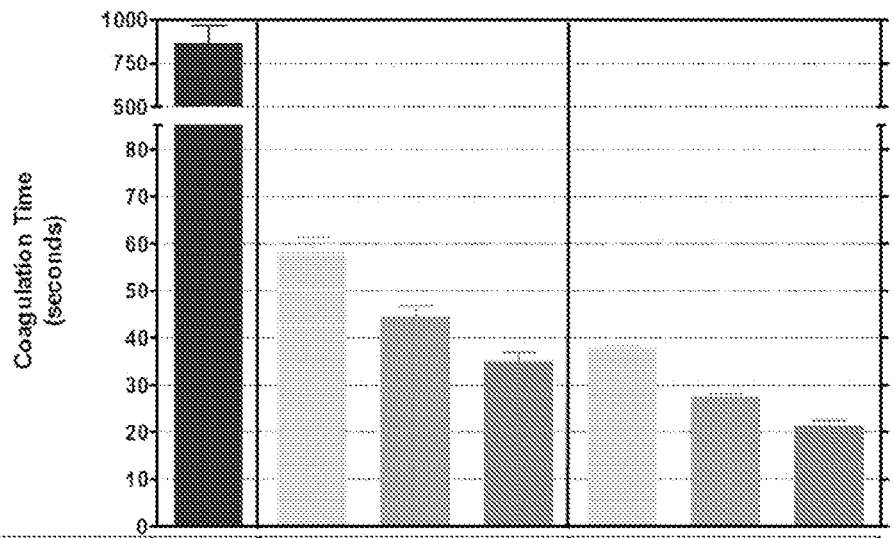
FIG. 8. TT-173 clotting activity in whole blood and effect of PS. The ability of TT 173 containing or not PS (0.1 mM) to coagulate healthy plasma and whole blood samples was tested. A) Aliquots (10 μl) of TT 173 and TT 173 incubated for 2 h with PS (final concentration 0.1 mM) were added to warmed cuvettes containing 130 μl of normal platelet-poor plasma. Immediately after, 20 μl of calcium chloride (100 mM) were added, and the time of coagulation (in seconds) was determined with the aid of a coagulometer. (Pool of plasma from 5 donors). B) Aliquots (200 μL) of TT-173 or TT-173+PS (0.1 mM) containing the amount of rTF represented in the figure, were added to aliquots (800 μL) of blood recently extracted from healthy donors. Coagulation time was measured with the aid of a chronometer from the beginning of the blood extraction until a stable and well consolidated clot appeared. N=3.
Figure 8:
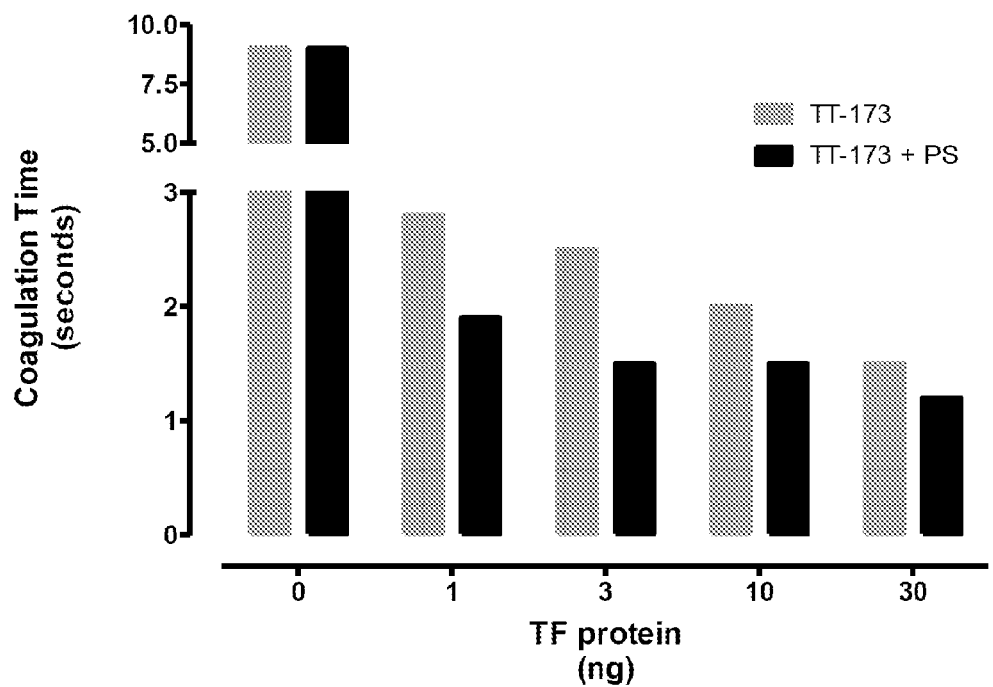

However, when the same TT-173 samples were tested for procoagulant activity in either normal plasma (FIG. 8, panel A) or normal whole blood (FIG. 8, panel B) a highly significant increment in clotting activity was observed when PS was associated to TT-173.

Therefore, the stimulatory effect of PS on TT-173 activity should be attributable to an effect on the coagulation cascade downstream than the initial TF:FVII interaction. Our interpretation is that PS modifies TT-173 vesicle surface, providing a PS-dependant scaffold similar to the one observed in activated platelets.

2.2. Mechanisms of Action of TT-173 and TT-173 PS

During normal hemostasis, the time required to attain the activation stage (time needed to reach the thrombin concentration required to activate FV, FVIII and platelets) is 4 minutes, approximately. This is the time required to allow the interaction between TF and FVII molecules, both present in a relatively low concentration either in plasma or in the membrane of damaged cells. Molecular collision and the resulting interaction between TF and FVII lead the transformation of FX into FXa which, in turn, produces thrombin.

Therefore, increasing the concentration of TF incorporated into a suitable membrane, such as by adding TT-173 to plasma or blood will increase the opportunity for interactions between TF and FVII to take place. This results in a much faster and higher production of FXa, and hence a faster production of the amount of thrombin required for the activation of platelets, FVIII and FV.

Figure 9:
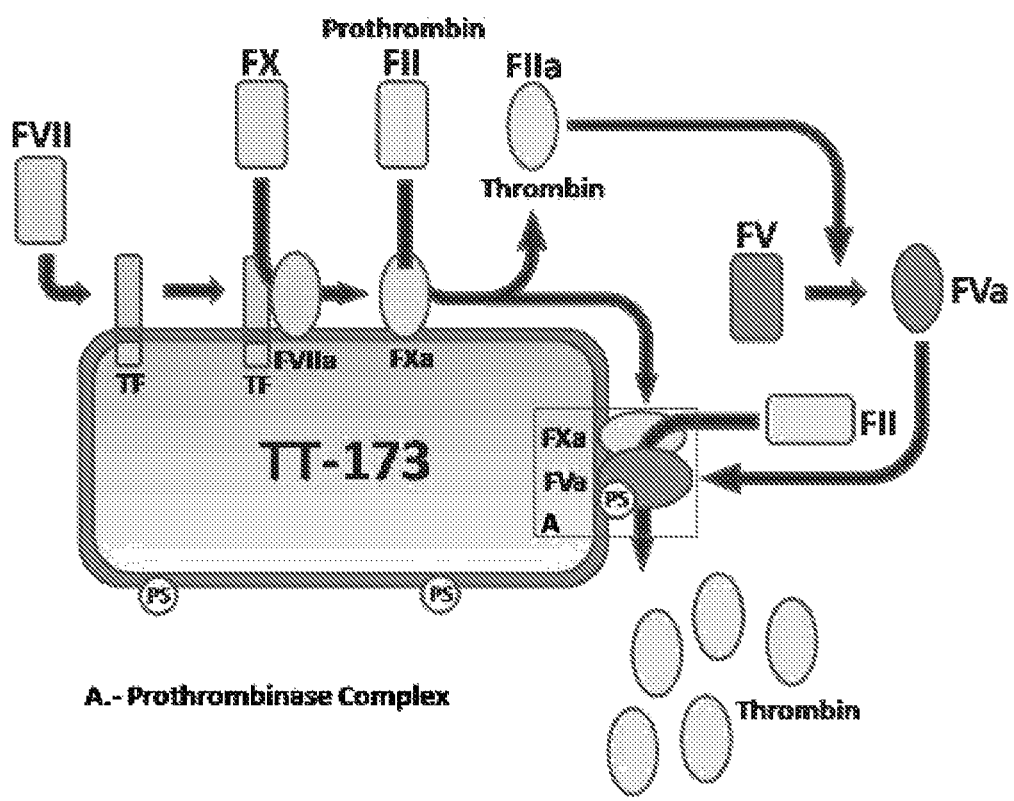
FIG. 9. Postulated mechanism of action of TT-173

In TT-173, TF is inserted into a membranous compartment also bearing discrete patches of PS. Thus, the addition of TT-173 to plasma or blood provides not only the initiator of the coagulation cascade at a higher concentration, but also a suitable surface that provides the appropriate, PS-containing, physiological scaffold for the formation of active prothrombinase complexes. FIG. 9 summarizes the proposed mechanism of action of TT-173.

During normal blood coagulation, the activation of coagulation takes approximately four minutes. This is a consequence of the relatively low concentration of TF protein in the damaged tissues adjacent to blood vessels, and the scarce amount of FVIIa circulating in the blood stream.

Figure 10:
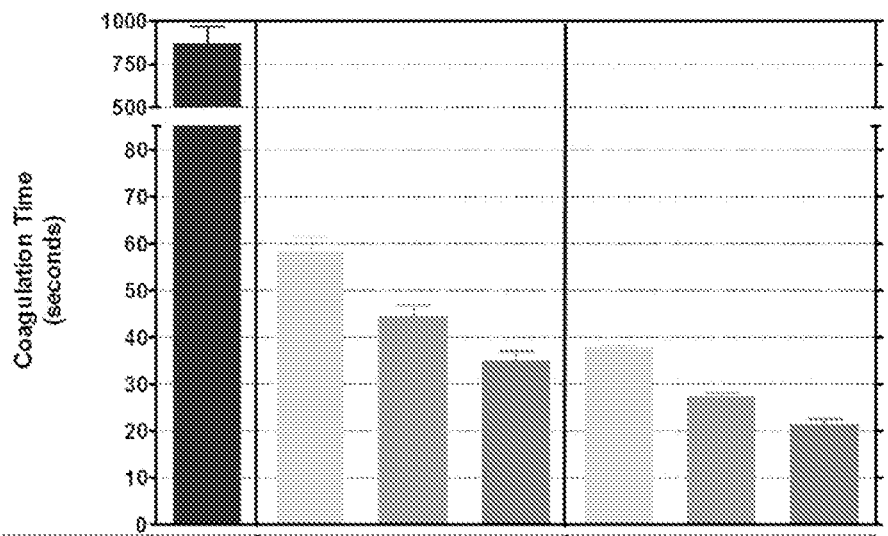
FIG. 10. TT-173 clotting activity in plasma deficient in coagulation factors VIII, IX or XI. (A) Aliquots (10 μl) of TT 173 or TT 173+PS (0.1 mM) were added to warmed cuvettes containing 130 μl of normal platelet-poor plasma, immediately afterwards 20 μl of calcium chloride (100 mM) were added, and the time of coagulation (in seconds) was determined with the aid of a coagulometer. (Pool of plasma from 5 donors). (B) Similar aliquots (10 μl) as described in A were added to warmed cuvettes containing 130 μl of factor-VIII, factor IX or factor XI depleted plasmas. Immediately afterwards 20 μl of calcium chloride (100 mM) were added, and the time of coagulation (in seconds) was determined with the aid of a coagulometer. (N=3).
Figure 10:
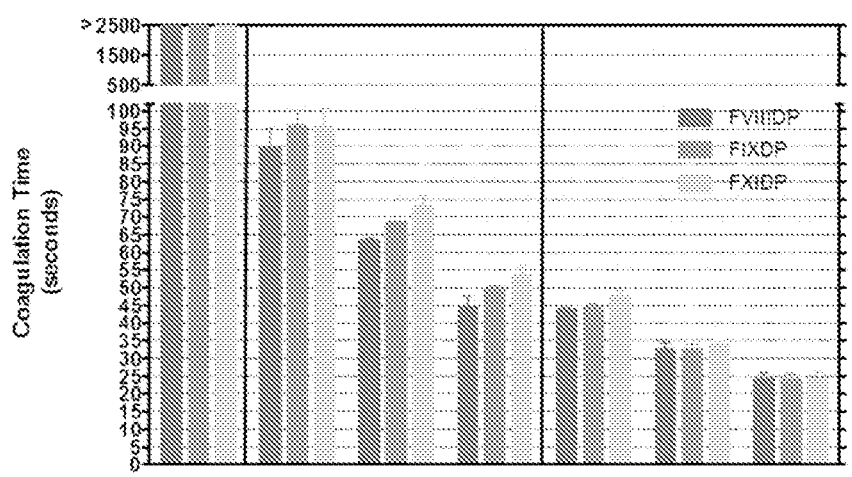
Figure 11:
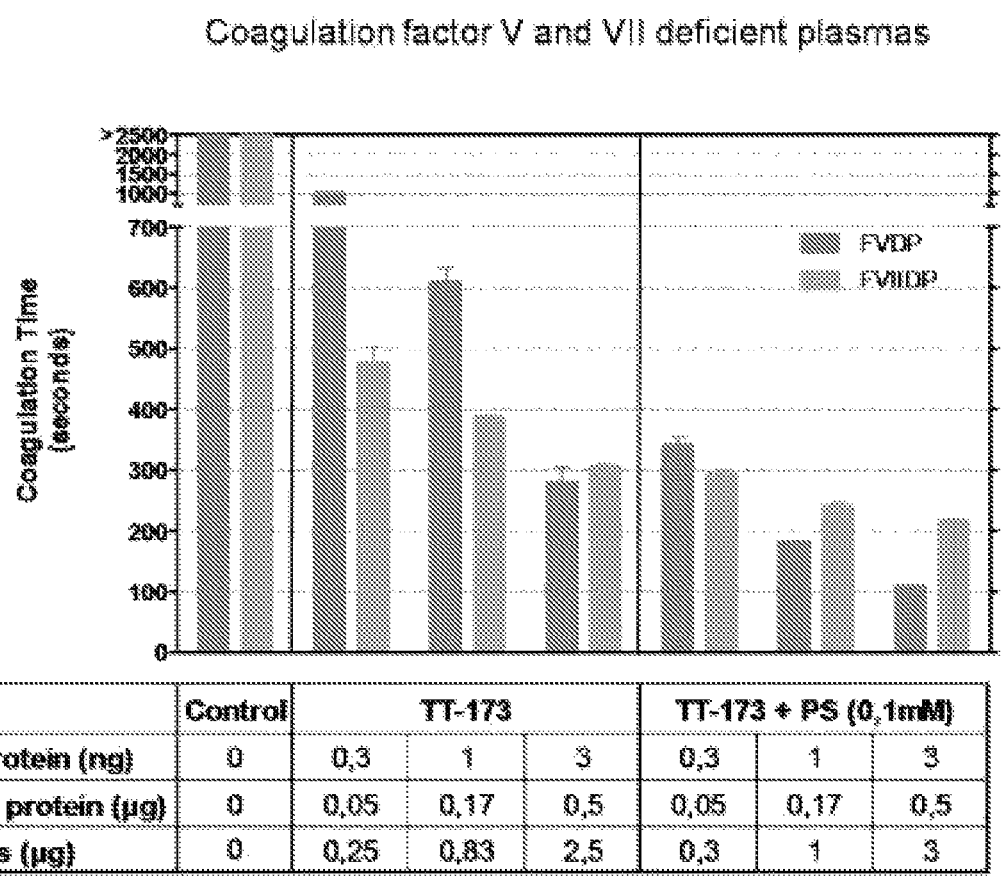
FIG. 11. TT-173 clotting activity in plasma deficient in coagulation factors V or VII. Aliquots (10 μl) of TT 173 or TT 173+PS (0.1 mM) were added to warmed cuvettes containing 130 μl of factor V or factor VII depleted plasmas. Immediately afterwards 20 μl of calcium chloride (100 mM) were added, and the time of coagulation (in seconds) was determined with the aid of a coagulometer. (N=3).
Figure 12:
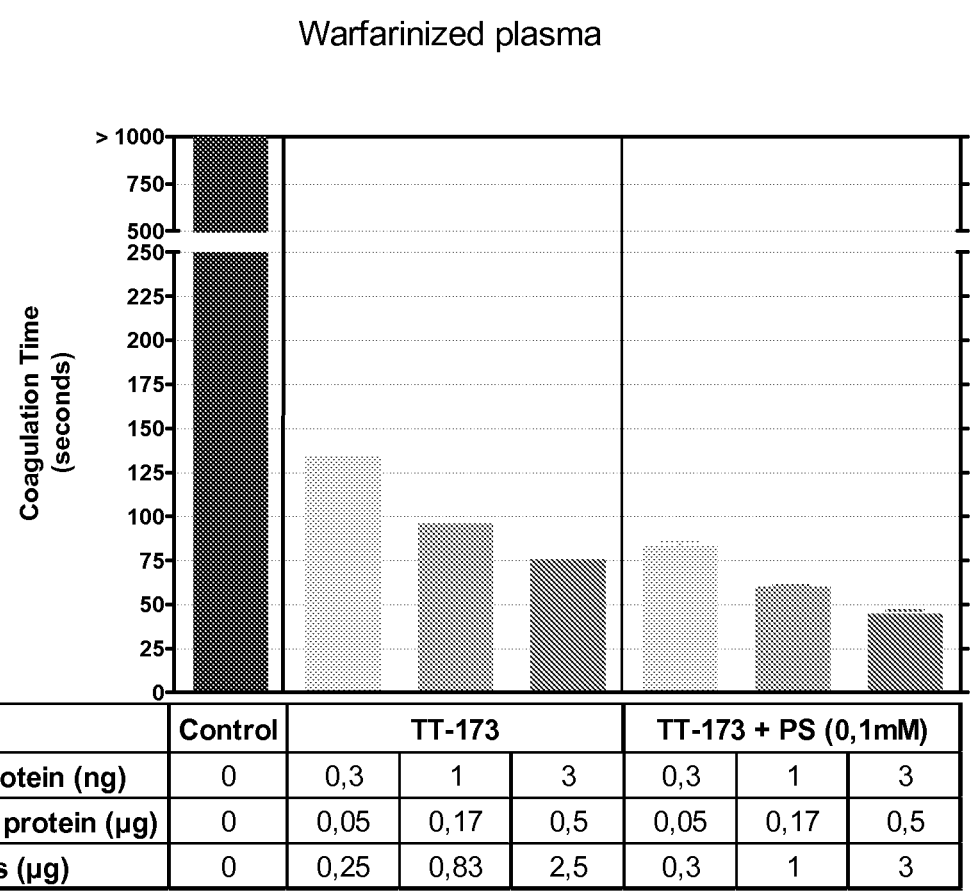
FIG. 12. TT-173 clotting activity in warfarin-treated plasma. Aliquots (10 μl) of TT 173 or TT 173+PS (0.1 mM) were added to warmed cuvettes containing 130 μl of factor V or factor VII depleted plasmas. Immediately afterwards 20 μl of calcium chloride (100 mM) were added, and the time of coagulation (in seconds) was determined with the aid of a coagulometer. (N=3).

This model, in which production of FXa is increased, explains the dramatic reduction in clotting time observed when TT-173 with or without PS is added to normal plasma (FIG. 10, left). Moreover, through the formation of prothrombinase complexes, the model explains the normal coagulation times observed when FVIII or FIX (deficiencies in Hemophilia A and B) are absent or in very low concentrations (FIG. 10, right). In the case of deficiencies in coagulation factors, addition of PS to TT-173 clearly decreases the clotting time. This effect is more evident in plasmas in which concentration of FVII or FV is less than 1% (FIG. 11).

As the model predicts, coagulation time of plasma with acquired deficiencies in FVII and FX, as effects of warfarin treatment, is also normalized by addition of TT-173 (FIG. 10).

2.3. Role of Yeast Membranes in TT-173 Activity

Figure 13:
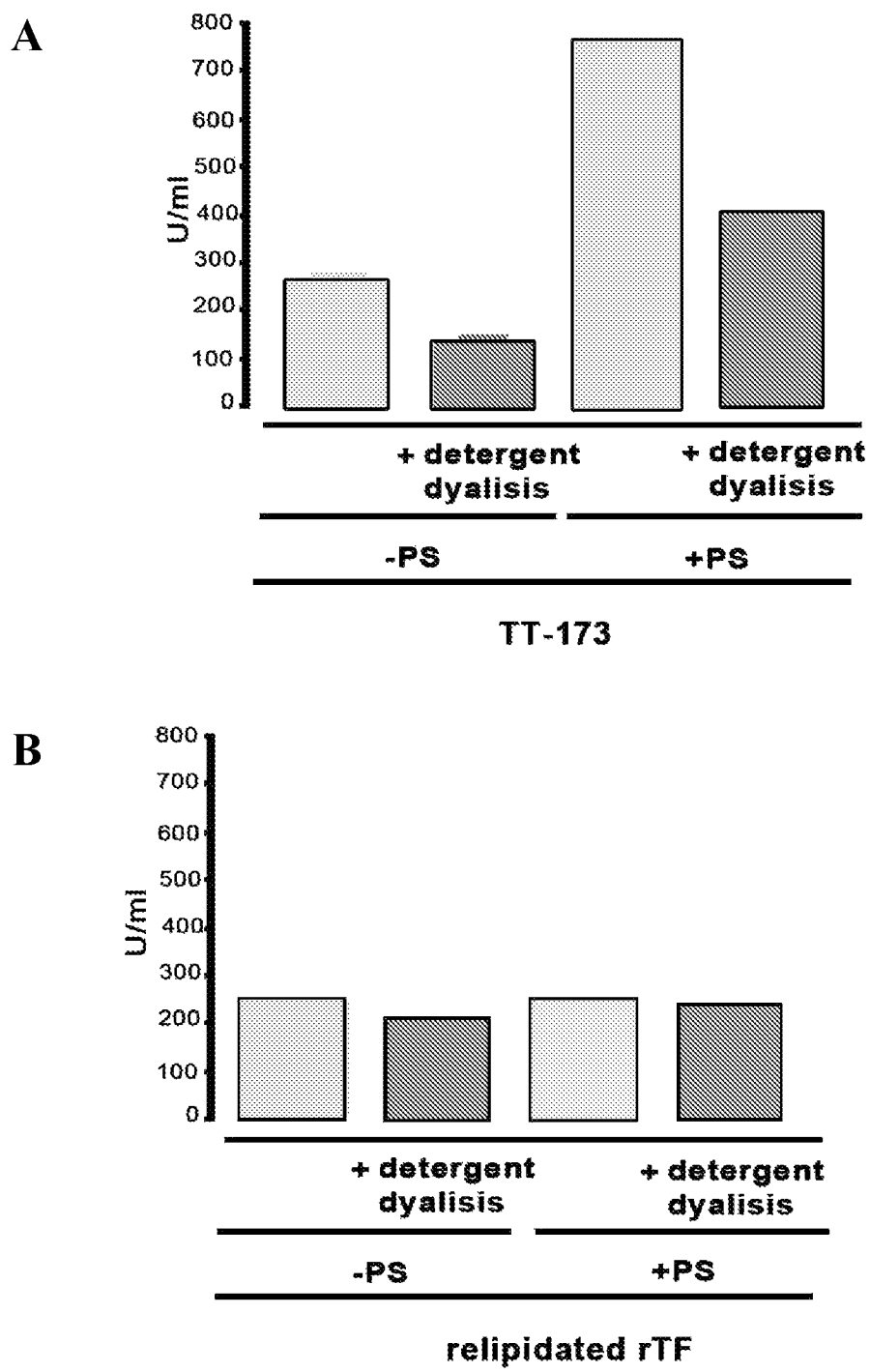
FIG. 13. Effect of reconstitution of TT-173 in the procoagulant activity. When TT-173 vesicles with and without added PS were broken apart by treatment with a dialyzable detergent, and then reconstituted in vitro by dialysis, approximately 50% of the initial activity was lost (panel A). However, when a similar experiment was done using relipidated rTF vesicles, no appreciable difference was observed before and after dialysis (panel B).

Yeast vesicles components exhibited a limited procoagulant activity by themselves, but all of them should be essential to maintain the integrity of the microparticles. When TT-173 vesicles with and without added PS were broken apart by treatment with a dialyzable detergent, and then reconstituted in vitro by dialysis, approximately 50% of the initial activity was lost (FIG. 13, panel A). However, when a similar experiment was done using relipidated rTF vesicles, no appreciable difference was observed before and after dialysis (FIG. 13, panel B).

This result indicates that clotting activity resides not only in the relative amounts of rTF, yeast proteins and yeast lipids, but also in the spatial disposition/orientation of all these components. When vesicles were produced spontaneously in vitro, all membrane components of TT-173 were incorporated randomly into newly formed membranes, and did not acquire the complex conformation that can only be acquired in the context that a eukaryotic live cell can provide.

Example 3

Production of a Pro-Coagulant Product Based on the Expression of the Full-Length TF Protein in Insect Cells 3.1 Construction of Recombinant Baculoviruses The construction of recombinant Baculoviruses (rBV) expressing the full-length of the mature human Tissue factor (TF) was performed as follows:

The cDNA coding for the mature human TF protein (aa 33-295) was amplified as a 816-bp fragment by polymerase chain reaction (PCR). For this PCR reaction, plasmid pTT-103, containing the TF coding gene, was used as a template, and oligonucleotides A 5'-CCGCTCGAGCGGTTATGAAA-CATTCAGTGGGGAGTTCTC-3' (SEQ ID NO: 7) and B 5'-CCGCTCGAGCGGTTATTCTCTGAATTC-CCCTTTCTC-3' (SEQ ID NO: 8), annealing respectively at 5' or 3'end of TF gene, were use as primers. The DNA fragment obtained was digested with NcoI and HindIII and inserted into the baculovirus transfer vector pFastBac1-mAV-MCS digested with the same restriction enzymes. The resulting plasmid, pFB-TF, was subjected to nucleotide sequencing to asses the correctness of the inserted TF sequence, and it was then used to produce the corresponding rBV by using the Bac-to-Bac system and by following the manufacturer's instructions (Invitrogen). For production and purification of active TF-containing vesicles, insect high five cells were infected with rBV expressing TF at a multiplicity of 5 PFU/cell. Cells were harvested at 72 hr post-infection, washed twice with phosphate-buffered saline, resuspended in lysis buffer (50 nM Tris-HCl, pH 8.0, 500 mM NaCl). Thereafter, cell extracts were disrupted with the aid of a dounce homogenizer. Aliquots of cell extracts were tested for clotting activity following the protocol described previously in Example 2. Table 2 shows the clotting activity elicited by the extracts.

TABLE 2

Coagulation time and TF protein concentration of control vesicles, recombinant TF, in vitro lipidated TF and TT-172 (insect cells-derived microvesicles carrying wt-TF).

|  | Coagulation time (seconds) | | TF protein (ng/ml) |
|---|---|---|---|
| Control | >300 | >300 | 0 |
| rTF | >300 | >300 | 30 |
| Lipidated rTF | 60.8 | 60.8 | 30 |
| TT-172 | 55.9 | 55.3 | 30 |

Figure 14:
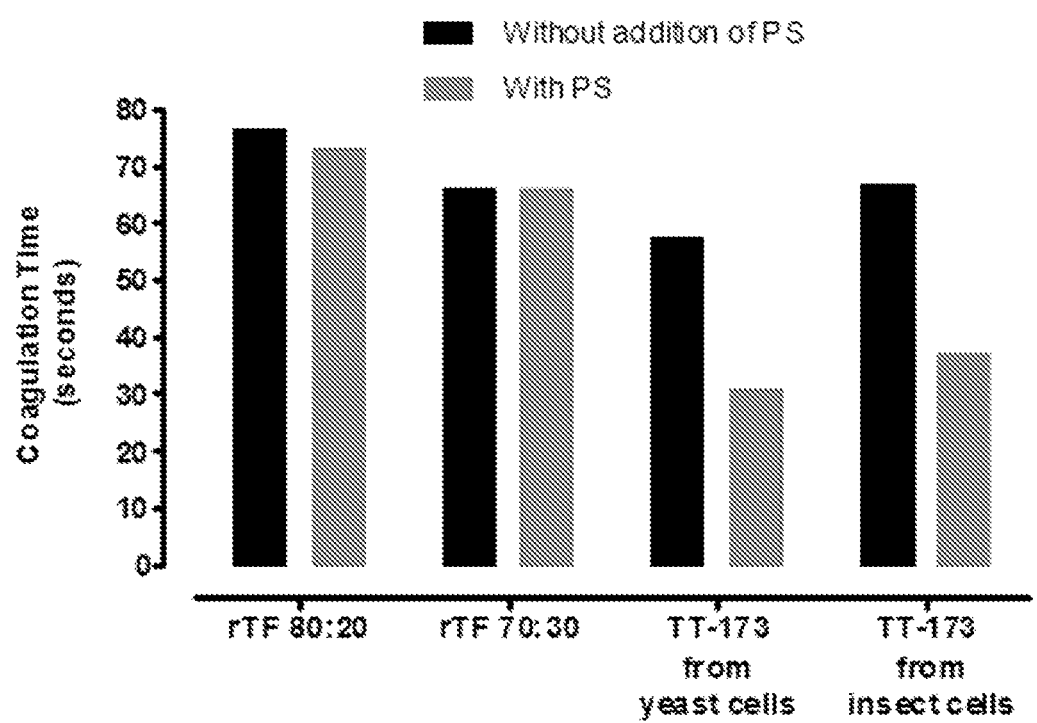
FIG. 14. Effect of addition of PS over different rTF-containing vesicles. Two aliquots (2 mL each) from either: i) relipidated rTF at a PC:PS concentration ratio of 80:20, ii) relipidated rTF at a PC:PS concentration ratio of 70:30, iii) TT-173 vesicles isolated from recombinant yeast expressing TF or iiii) TT-173 vesicles isolated from insect cells infected with a recombinant baculovirus expressing were prepared at 4° C. PS at a concentration of 0.1 mM was added to one of the aliquots of each of the rTF-containing vesicles, and incubated at R/T for 2 h. During this time, the other aliquot was kept at 4° C. After that, both aliquots from each rTF-containing vesicles were tested for prociagulant activity as described in figure legend 1.

3.2. Effect of Phosphatydilserine (PS) on TT-173 Insect Cells-Derived Microvesicles Carrying wt-TF) Bioactivity To provide further evidence that the effect observed and claimed in this patent is restricted to eukaryotic-derived structures, and could not be recreated in artificially-made vesicles by relipidation, PS was added at concentration 0.1 mM to aliquots with equivalent clotting activity of either TT-173 vesicles produced in yeast cells, TT-172 vesicles produced in insect cells or in vitro relipidated rTF at PC:PS ratios of 80:20 and 70:30. After incubation of the different vesicles with PS for 2 h at R/T, samples from the different rTF-containing products were tested for their clotting activity. The results are shown in FIG. 14. As observed, addition of PS to TT-170 from in insect cells origin resulted in a decrease in the clotting time similar to that obtained with yeast cells, clearly reduced the clotting time. However, as expected, addition of PS to relipidated rTF did not result in an appreciable increase in procoagulant activity, at any of the PC:PS proportions used for relipidation.

Example 4

Figure 15:
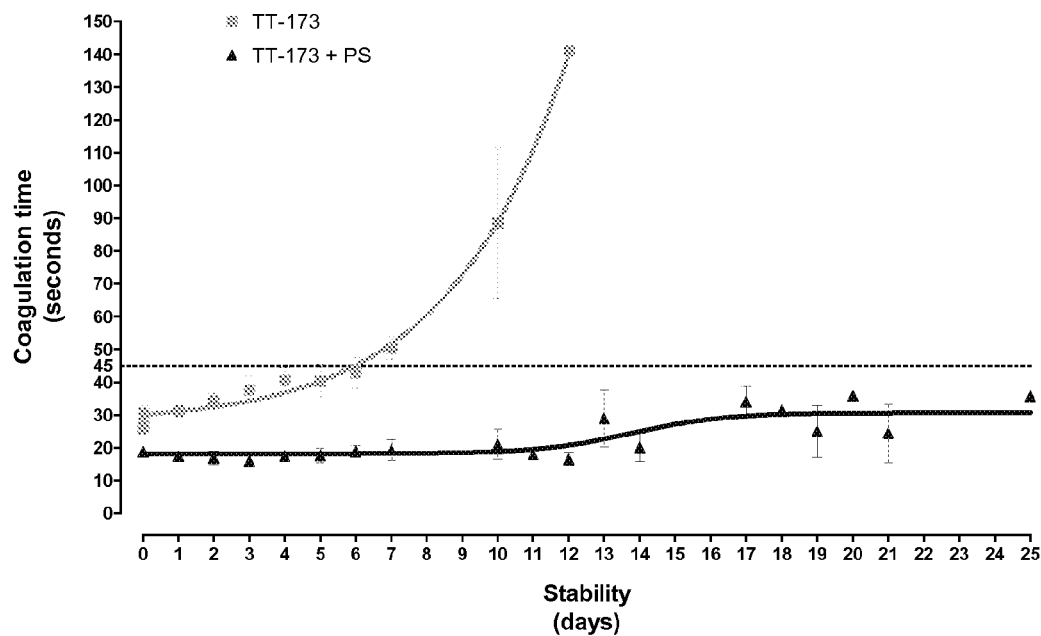
FIG. 15. Addition of PS provides stability to TT-173 vesicles. Four aliquots, 10 mL each, from three independent lots of TT-173 were used in this study. Two aliquots from each lot were incubated with PS (0.1 mM) at R/T for two hours, and the rest of aliquots were kept at 4° C. After this time, 10 μL from each of the twelve TT-173 samples were used to determine the clotting activity (time 0), following the procedure described in the legend of FIG. 1. Immediately after, half of the aliquots (3 of TT-173−PS, and 3 of TT-173+PS each of them corresponding to one of the three lots) were maintained at 4° C. during the rest of the stability experiment, and the rest (3 of TT-173−PS, and 3 of TT-173+PS) were kept at 20° C. At the indicated times in the figure, 10 μl from each aliquot were used to determine clotting activity in either the aliquots kept at 4° C. (A) or at 20° C. (B). Results are plotted with the standard deviation. The means of minimum stability among different batches at 4° C. (C) and 20° C. (D) at is also shown FIG. 16. Addition of FVII, FVIIa, FX and FXa amplifies the procoagulant effect of TT-173. Different concentrations of FVII (20 nM and 60 nM), FVIIa (20 nM and 60 nM), FX (1000 nM and 3000 nM) and FXa (1000 nM) were added to TT-173+PS 0.1 (mM). Aliquots of the TT-173+PS 0.1 (mM)/FVII, TT-173+PS 0.1 (mM)/FVIIa, TT-173+PS 0.1 (mM)/FX and of the TT-173+PS 0.1 (mM)/FXa mixtures were checked for clotting activity in a standard coagulometric assay at a final concentration of TF in plasma of 45 ng/ml. As it is shown, addition of FVII, FVIIa and FX reduces coagulation time in approximately 2 s and that addition of FXa reduces coagulation time in approximately 7 s.
Figure 15:
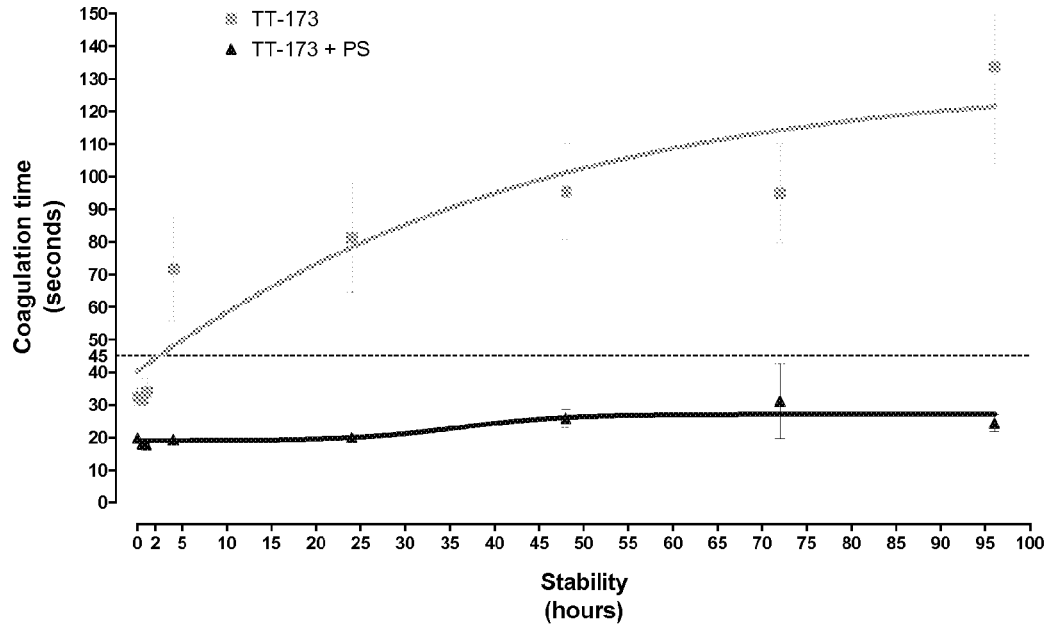
Figure 15:
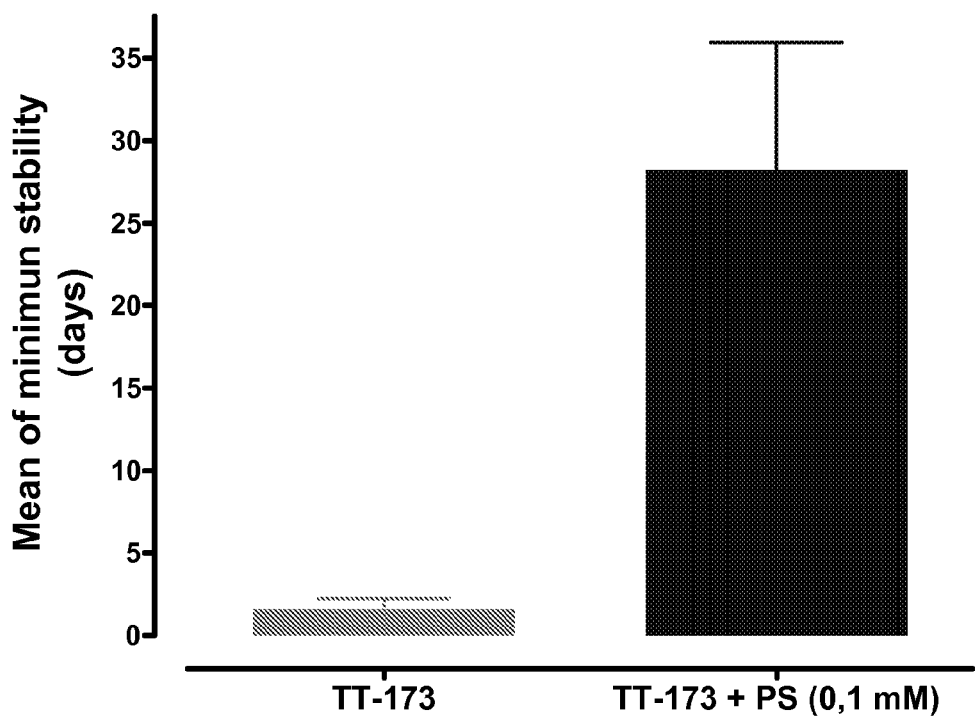
Figure 15:
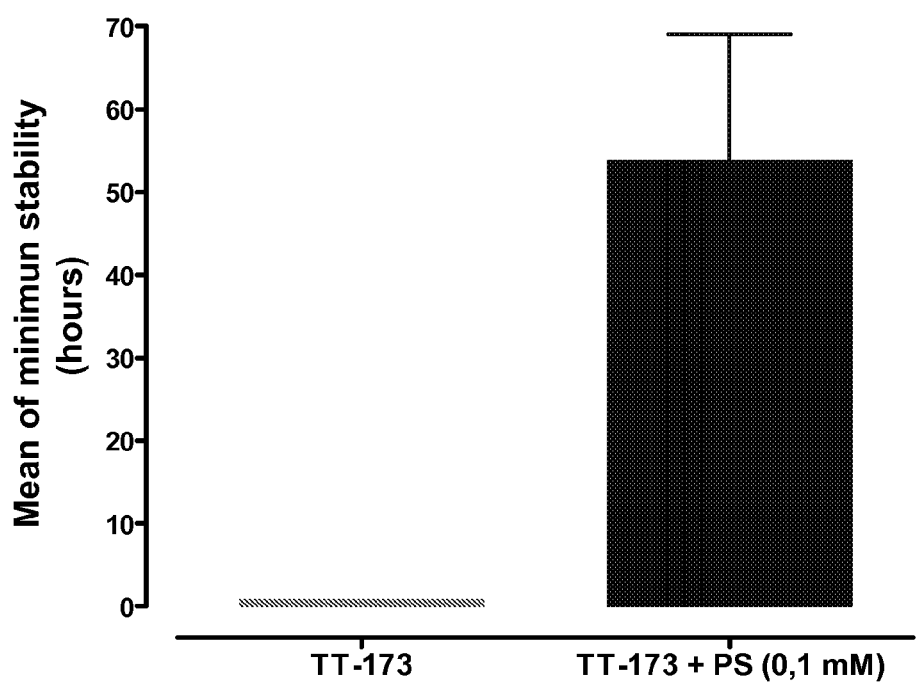

Another unexpected effect of PS addition was its incidence over the stability of TT-173 vesicles. To test this effect, aliquots from three independent TT-173 lots incubated or not with PS as described in example 2 were maintained at two different temperatures (4° C. and 20° C.) for a prolonged period of time. At different time points, an aliquot from each sample was analyzed for clotting activity. The result of this experiment is shown in FIG. 15. As shown above, the addition of PS over TT-173 samples accelerates coagulation time up to 10 seconds at time 0, and unexpectedly, the stability of samples containing PS was prolonged in comparison with samples without PS. This stability effect was especially evident at 20° C., while TT-173 samples without extra PS lost more than 50% of activity after 5 h, samples in which PS was added remained stable for at least 4 days.

The mean of minimum stability of different batches of TF-173 with or without added PS was then determined at 20° C. and 4° C.

|  | Stability at 20° C. (hours) | |
|---|---|---|
| Batch | TT-173 | TT-173 + PS (0.1 mM) |
| TT-173 612-615 | 1 | 96 |
| TT-173 644-647 | 1 | 48 |
| TT-173 660-663 | 1 | 24 |
| TT-173 702-705 | 1 | 48 |
| Mean of minimum stability | 1 | 54 |

|  | Stability at 4° C. (hours) | |
|---|---|---|
| Batch | TT-173 | TT-173 + PS (0.1 mM) |
| TT-173 612-615 | <1 | 25 |
| TT-173 628-631 | 4 | <57 |
| TT-173 644-647 | <1 | <28 |
| TT-173 660-663 | <1 | 20 |
| TT-173 702-705 | <1 | >11 |
| Mean of minimum stability | 1.6 | 28.2 |

The mean minimum stability is shown in FIG. 15 (panels C and D).

Example 5

Enhancement of the Pro-Coagulant Effect of TT-173 by Pro-Coagulant Agents

Figure 16:
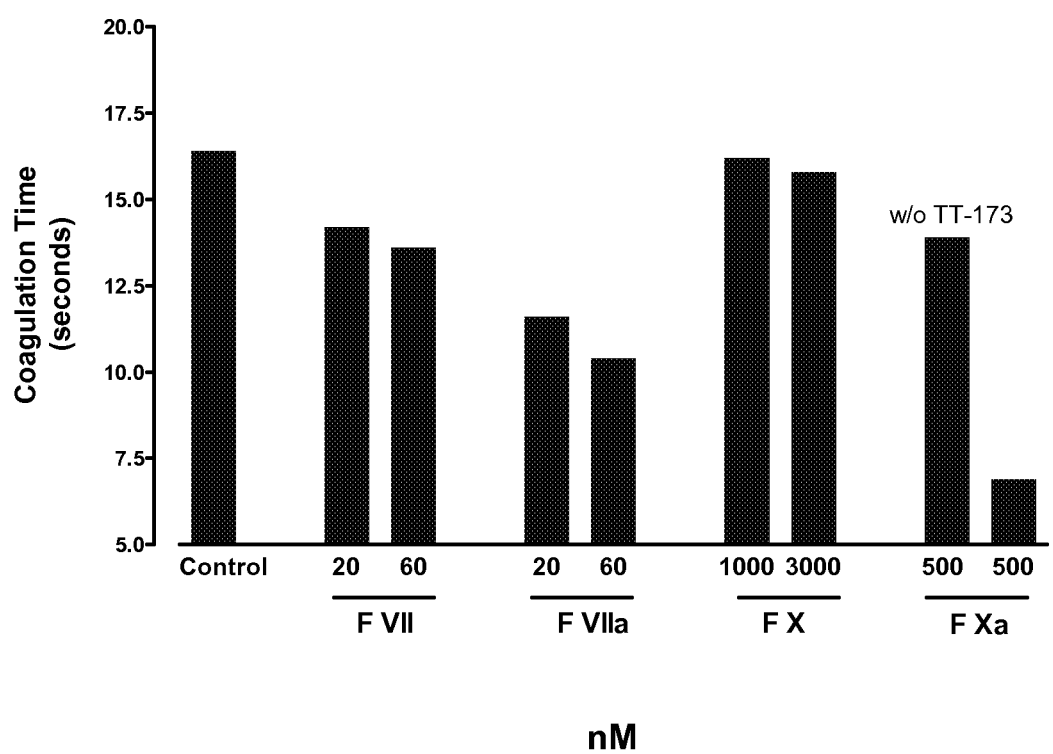

Different concentrations of FVII (20 nM and 60 nM), FVIIa (20 nM and 60 nM), FX (1000 nM and 3000 nM) and FXa (1000 nM) were added to TT-173. At different time points, starting from the time in which PS was added (time 0), aliquots of the TT-173/FVII and of the TT-173/FX mixtures were checked for clotting activity in a standard coagulometric assay. The results, presented in FIG. 16, clearly show that addition of FVII, FVIIa and FX reduces coagulation time in approximately 2 s and that addition of FXa reduces coagulation time in approximately 7 s.

The invention claimed is:

1. A method for the preparation of a TF-bearing microvesicle having pro-coagulant activity comprising:
   (i). expressing TF or a variant thereof having pro-coagulant activity in an eukaryotic cell selected from a yeast, plant or insect cell;
   (ii). lysing the TF-expressing cells of step (i) in the absence of detergents or, when detergents are used, using concentrations of said detergents below the critical micellar concentration;
   (iii). recovering TF-bearing microvesicles from the lysed cells of step (ii) and
   (iv). contacting the vesicles obtained in step (iii) with a negatively charged phospholipid in the absence of detergents under conditions adequate for the incorporation of said phospholipid into said vesicles;
   wherein said microvesicles are formed by lipid membranes, or fragments thereof, from said eukaryotic cell.

2. A method according to claim 1, wherein the eukaryotic cell is a yeast cell.

3. A method according to claim 1, wherein the contacting step is carried out using 0.05 μmol of negatively charged phospholipids wherein the protein content of the microvesicles is lower than 50 microg and 0.1 μmol negatively charged phospholipids wherein the protein content of the microvesicles is higher than 50 microg.

4. A method according to claim 1, wherein the negatively charged phospholipid is selected from the group of a sphingosine-containing phospholipid or glycerol-containing phospholipid.

5. A method according to claim 4 wherein the glycerol-containing phospholipid is phosphatidylserine.

6. A method according to claim 1 wherein said TF or the variant thereof having pro-coagulant activity is glycosylated.

7. A method according to claim 1 wherein the TF is a mature TF protein, preferably, human mature TF protein.

8. A method according to claim 7 wherein the TF carries the N124A mutation and an hexahistidine tag at the C terminus.

9. A TF-bearing microvesicle obtained using the method of claim 1.

10. A pharmaceutical composition comprising a TF-bearing microvesicle according to claim 9 and a pharmaceutically acceptable vehicle.

11. A pharmaceutical composition according to claim 10 further comprising at least an agent that promotes the process by which blood forms clots.

12. A pharmaceutical composition according to claim 10 wherein the composition is lyophilised.

13. A method for the determination of prothrombin time in a sample using a TF-bearing microvesicle as defined in claim 9; the method comprising adding a TF-bearing microvesicle to a sample and, determining the prothrombin time in the sample.

14. A kit for the determination of prothrombin time comprising a microvesicle as defined in claim 9.

15. A method for the treatment of a haemorrhage, for promoting wound healing or for the treatment of an angiogenesis-related disease, the method comprising administering a TF bearing microvesicle as defined in claim 9 in a subject in need thereof.

16. A method according to claim 15, wherein the haemorrhage is treated in a subject selected from the group of a healthy subject and a subject with a hemorrhagic diathesis, where said hemorrhagic diathesis is selected from the group of a congenital coagulopathy, an acquired coagulopathy, a platelet disorder and a combination thereof.

17. A method according to claim 16, wherein the TF-bearing microvesicle is administered topically.

* * * * *